US008137975B2

(12) United States Patent
Mylvaganam et al.

(10) Patent No.: US 8,137,975 B2
(45) Date of Patent: Mar. 20, 2012

(54) METHOD FOR A RAPID ANTIBODY-BASED ANALYSIS OF PLATELET POPULATIONS

(75) Inventors: Ravindra Mylvaganam, Longmeadow, MA (US); Ronald D. Paul, Fort Lauderdale, FL (US)

(73) Assignee: Beckman Coulter, Inc., Brea, CA (US)

( * ) Notice: Subject to any disclaimer, the term of this patent is extended or adjusted under 35 U.S.C. 154(b) by 421 days.

(21) Appl. No.: 12/260,734

(22) Filed: Oct. 29, 2008

(65) Prior Publication Data

US 2009/0111118 A1    Apr. 30, 2009

Related U.S. Application Data

(60) Provisional application No. 60/983,309, filed on Oct. 29, 2007.

(51) Int. Cl.
*G01N 31/00* (2006.01)
*G01N 33/00* (2006.01)

(52) U.S. Cl. ....... 436/10; 435/7.21; 435/7.24; 435/7.25; 435/285.2; 435/287.2; 435/288.7; 435/962; 435/973; 436/56; 436/164; 436/172; 422/68.1; 422/73; 422/82.01; 422/82.02; 422/82.08; 422/82.09; 422/430

(58) Field of Classification Search ............. 435/2, 7.21, 435/7.24, 7.25, 285.2, 287.2, 288.7, 962, 435/973; 436/521, 522, 10, 56, 63, 164, 436/172, 175; 422/61, 73, 82.01, 82.02, 422/82.08, 82.09, 68.1, 430
See application file for complete search history.

(56) References Cited

U.S. PATENT DOCUMENTS 3,962,125 A    6/1976 Armstrong
(Continued)

FOREIGN PATENT DOCUMENTS

EP    0317156    5/1989
(Continued)

OTHER PUBLICATIONS

Matic et al., Whole blood analysis of reticulated platelets: improvements of detection and assay stability, Cytometry, 34 (5) 229-234 (Oct. 1998).*

(Continued)

*Primary Examiner* — Gail R Gabel
(74) *Attorney, Agent, or Firm* — K&L Gates LLP; Louis C. Cullman; Dean G. Stathakis

(57) ABSTRACT

A method for identifying a platelet population, preferably a population of immature, reticulated platelets, in a biological sample involves incubating the biological sample for less than 5 minutes with at least one labeled, ligand (e.g., monoclonal antibody) that binds to an epitope or antigen on platelets and with a nucleic acid dye. In one embodiment, the dye is Acridine Orange and the label on the ligand is PE-Cy7. The sample is then analyzed and one or more platelet populations is rapidly identified or quantified by passing the incubated sample through a sensing region of a flow cytometer. In one embodiment, this method occurs without a washing or physical cell separation step. The incubated sample is irradiated with a laser light source, and fluorescence of the labeled ligand and the nucleic acid dye are measured along with at least one additional parameter, e.g., light scatter, direct current, axial light loss, opacity, radio frequency, and fluorescence. These parameters are used to identify qualitatively or quantitatively the platelet populations in the sample. This rapid analytic method is particularly valuable in clinical situations where either low platelet counts or interfering conditions lead to inaccuracies of the platelet measurement. This method is suitable for performance in an automated hematology analyzer.

22 Claims, 8 Drawing Sheets

U.S. PATENT DOCUMENTS

| | | | |
|---|---|---|---|
| 5,030,554 | A | 7/1991 | Quintana |
| 5,047,321 | A | 9/1991 | Loken |
| 5,064,616 | A | 11/1991 | Brosnan |
| 5,125,737 | A | 6/1992 | Rodriguez |
| 5,137,809 | A | 8/1992 | Loken |
| 5,164,311 | A | 11/1992 | Gupta |
| 5,234,816 | A | 8/1993 | Terstappen |
| 5,438,003 | A | 8/1995 | Colella |
| 5,563,070 | A | 10/1996 | Yamamoto |
| 5,565,499 | A | 10/1996 | Klemarczyk |
| 5,631,165 | A | 5/1997 | Chupp |
| 5,633,167 | A | 5/1997 | Fan |
| 5,648,225 | A | 7/1997 | Kim |
| 5,763,280 | A | 6/1998 | Li |
| 5,776,709 | A | 7/1998 | Jackson |
| 5,812,419 | A | 9/1998 | Chupp |
| 5,882,933 | A | 3/1999 | Li |
| 6,060,322 | A * | 5/2000 | Horton et al. ............ 436/63 |
| 6,197,593 | B1 | 3/2001 | Deka |
| 6,228,532 | B1 | 5/2001 | Tsuji |
| 6,228,652 | B1 | 5/2001 | Rodriquez |
| 6,287,791 | B1 | 9/2001 | Terstappen |
| 6,461,825 | B1 | 10/2002 | Carriere |
| 6,573,102 | B2 | 6/2003 | Li |
| 6,692,968 | B2 | 2/2004 | Burshteyn |
| 6,900,023 | B1 | 5/2005 | Houwen |
| 6,911,313 | B2 | 6/2005 | Houwen |
| 7,674,598 | B2 * | 3/2010 | Paul et al. ............ 435/7.21 |
| 2003/0138851 | A1 | 7/2003 | DeMatos |
| 2005/0260766 | A1 | 11/2005 | Paul |
| 2006/0269970 | A1 | 11/2006 | Paul |
| 2007/0202549 | A1 | 8/2007 | Ahearn |

FOREIGN PATENT DOCUMENTS

| | | |
|---|---|---|
| EP | 1363126 | 11/2003 |
| WO | 2005/017184 A2 | 2/2005 |

OTHER PUBLICATIONS

Saxonhouse et al., Reticulated platelet percentages in term and preterm neonates, J. Pediatric Hematology Oncology, 26 (12): 797-802 (Dec. 2004).*

Ault et al, The significance of platelets with increased RNA content (reticulated platelets). A measure of the rate of thrombopoiesis, American J Clinical Pathology, vol. 98, (Dec. 1992), pp. 637-646.

Balduini et al, Relationship between size and thiazole orange fluorescence of platelets in patients undergoing high-dose chemotherapy, British J Haematology, vol. 106, No. 1, (Jul. 1999), pp. 202-207.

Bonan et al, Determination of the percentage of thiazole orange (TO)-positive, "reticulated" platelets using autologous erythrocyte TO fluorescence as an internal standard, Cytometry, vol. 14, No. 6, (1993), pp. 690-694.

Briggs et al, Assessment of an immature platelet fraction (IPF) in peripheral thrombocytopenia., British J Haematology, vol. 126, No. 1, (Jul. 2004), pp. 93-99.

Chaoui et al, Reticulated platelets: a reliable measure to reduce prophylactic platelet transfusions after intensive chemotherapy, Transfusion, vol. 45, No. 5, (May 2005), pp. 766-772.

Ingram et al, Reticulated platelets following acute blood loss, Brit J Haematology, vol. 17, No. 3, (Sep. 1969), pp. 225-229.

Kienast et al, Flow cytometric analysis of thiazole orange uptake by platelets: a diagnostic aid in the evaluation of thrombocytopenic disorders, Blood, vol. 75, No. 1, (Jan. 1, 1990), pp. 116-121.

Lee et al, Thiazole orange: a new dye for reticulocyte analysis., Cytometry, vol. 7, No. 6, (Nov. 1986), pp. 508-517.

Matic et al, Whole blood analysis of reticulated platelets: improvements of detection and assay stability, Cytometry, vol. 34, No. 5, (Oct. 1998), pp. 229-234.

Rinder et al, Correlation of thrombosis with increased platelet turnover in thrombocytosis, Blood, vol. 91, No. 4, (Feb. 15, 1998), pp. 1288-1294.

Robinson et al, Flow cytometric analysis of reticulated platelets: evidence for a large proportion of non-specific labelling of dense granules by fluorescent dyes., Brit J Haematology, vol. 100, No. 2, (Feb. 1998), pp. 351-357.

Saxonhouse et al, Reticulated platelet percentages in term and preterm neonates, J Pediatric Hematology Oncology, vol. 26, No. 12 (Dec. 2004), pp. 797-802.

Schmitz et al, Optimization of flow-cytometric discrimination between reticulocytes and erythrocytes., Cytometry, vol. 7, No. 5, (Sep. 1986), pp. 439-444.

Seligman et al, Automated analysis of reticulocytes using fluorescent staining with both acridine orange and an immunofluorescence technique, American J Hematology, vol. 14, No. 1, (Feb. 1983), pp. 57-66.

Shapiro, HM, ed., Nucleic Acid Dyes and their Uses. In Practical Flow Cytometry, 4th Edition, NJ, John Wiley & Sons, 2003, pp. 306-326.

Stohlawetz et al, Effects of endotoxemia on thrombopoiesis in men, Thrombosis and Haemostasis, vol. 81, No. 4, (Apr. 1999), pp. 613-617.

Watanabe et al, Automated measurement of reticulated platelets in estimating thrombopoiesis., European J Haematology, vol. 54, No. 3, (Mar. 1995), pp. 163-171.

Weiland et al, Evaluation of the automatie immature granulocyte count (IG) on Sysmex XE-2100 automated hematology analyzer vs visual microscopy, Sysmex J. International, vol. 12, No. 2, (2002), pp. 63-70.

Fujimoto et al, Flow cytometric method for enumeration and classification of reactive immature granulocyte populations, Cytometry, vol. 42, (Dec. 2000), pp. 371-378.

Bowen et al, Abnormal patterns of expression of CD16 (FcRyIII) and CD11b (CRIII) antigens by developing neutrophils in the bone marrow of patients with myelodysplastic syndrome, Laboratory Hematology, vol. 3, (Oct. 1997), pp. 292-298.

Burgess et al, Counting absolute numbers of specific leukocyte subpopulations in avian whole blood using a single-step flow cytometric technique: comparison of two inbred lines of chickens, J. Immunological Methods, vol. 227, No. 1-2, (Jul. 30, 1999), pp. 169-176.

Civin et al, Cell surface antigens on human marrow cells: dissection of hematopoietic development using monoclonal antibodies and multiparameter flow cytometry, Intl. J. Cellular Cloning, vol. 5, (Jul. 1987), pp. 267-288.

Stockert et al, Cytochemistry of mast cells: new fluorescent methods selective for sulfated glycosaminoglycans, Acta Histochemistry, vol. 102, No. 3, (Aug. 2000), pp. 259-272.

Thomas et al, Combined optical and electronic analysis of cells with the AMAC transducers, J. Histochemistry and Cytochemistry, vol. 25, No. 7 (Jul. 1977), pp. 827-835.

Goossens et al, Preliminary data on the feasibility of bone marrow screening on the Sysmex XE-2100 automated hematology analyzer, Sysmex J. International, vol. 11, No. 2 (2001), pp. 70-73.

Macey et al. "The Q Prep System: Effects on the Apparent Expression of Leukocyte Cell Surface Antigens." Cytometry 30: 67-72 (1997).

Salvagno et al. "Evaluation of platelet turnover by flow cytometry." Platatelets, May 2006; 17(3): 170-177.

Schmitz et al. "European Working Group on Clinical Cell Analysis: Consensus Protocol for the Flow Cytometric Characterisation of Platelet Function." Thrombosis and Haemostasis, vol. 79, No. 5, May 1, 1998, pp. 885-896.

* cited by examiner

FIG. 5A
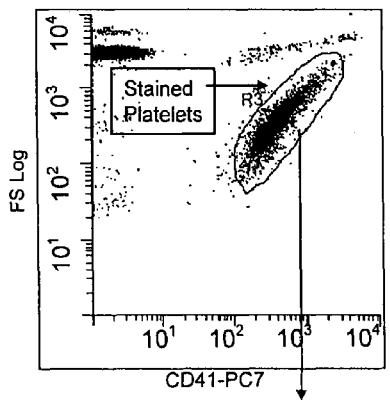
FIG. 5B
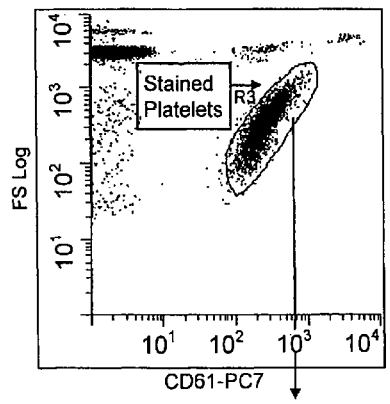
FIG. 5C
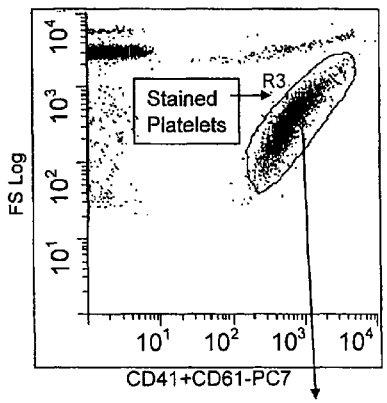
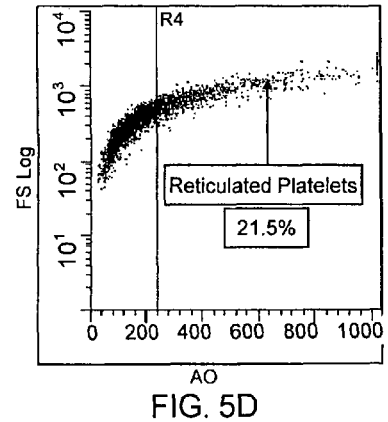
FIG. 5D
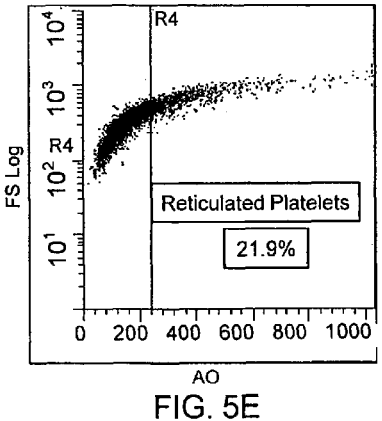
FIG. 5E
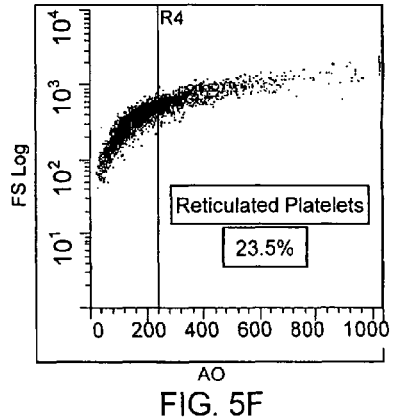
FIG. 5F

METHOD FOR A RAPID ANTIBODY-BASED ANALYSIS OF PLATELET POPULATIONS

BACKGROUND

Platelets, which play a role in hemostasis, are of three general types: megakaryocytes, reticulated (i.e., immature) platelets that are released into the peripheral blood following megakaryocytic fragmentation, and mature platelets. However, other subpopulations of platelets exist in the blood, which are commonly uncounted or miscounted in typical clinical analyses. Such 'subpopulations' include giant platelets (i.e., unusually large platelets), platelet clumps (i.e., multi-platelet combinations), and platelet satellites (i.e., adherence of platelets to leucocytes or other cells).

The differentiation and enumeration of these various types of blood cells and platelets in a patient's peripheral blood, the ratios thereof, as well as the determination of certain parameters or characteristics thereof, are necessary to permit diagnosis of a variety of hematological disorders or diseases. The absolute numbers, concentrations and relative percentages of the different types of platelets are highly indicative of the presence or absence and/or stage of certain disease states. For example, the measurement and enumeration of platelet types is important for the diagnosis and monitoring of a variety of disorders characterized by abnormal presence and/or numbers of platelets at various stages of maturation. For example, the identification and measurement of the platelet populations individually, the ratio thereof, as well as an accurate measurement of total platelet numbers including all subpopulations, has considerable clinical utility for monitoring thrombopoiesis and platelet turnover.

Typically, only mature cells are present in detectable amounts in peripheral blood. When a platelet count is suspiciously low, and/or the automated blood cell counter presents with a warning, a manual blood smear is typically the only way to determine whether or not there are adequate platelets present and to verify the presence of giant platelets, and/or platelet clumps. Manual counting involves contacting the cells with nucleic acid specific, non-metachromatic dyes (Kienast, J. and Schmitz, G. 1990 *Blood* 75: 116-121; Ault, K. A. et al, 1992 *Am J Clin Pathol* 98: 637-646; Robinson, M. S. C. et al, 1998 *Brit J Haematol* 100: 351-357) or nucleic acid specific, metachromatic dyes (Schmitz, F. J. and Werner, E., 1986 *Cytometry* 7: 439-444; and U.S. Pat. No. 6,060,322). Metachromatic dyes emit fluorescence over a broad range of wavelengths and are particularly useful for staining immature reticulated platelets, which contain RNA condensed as reticulum. For example, on histochemical staining with new methylene blue, the reticulum of immature platelets appears as patchy purplish-blue areas. Once stained, all the platelets are enumerated in a microscopic view, expressing the platelets containing the reticulum as a percentage of the total platelets and expressing them as a percentage of reticulated platelets (Ingram, M. and Coopersmith, A. 1969 *Brit J Haematol* 17: 225-228). This manual counting procedure is tedious, cumbersome and prone to human counting errors.

Another method of platelet analysis employs flow cytometry techniques, which are faster and more reliable. Such techniques generally employ the non-metachromatic dyes, thiazole orange (TO), auramine O, and polymethine with oxazine (Lee, L. G. et al, 1986 Cytometry 7: 508-517; Watanabe, K., et al, 1995 *Eur J Haematol* 54: 163-171; Briggs, C. et al, 2004 *Brit L Haematol* 126: 93-99). Acridine orange (AO), a metachromatic dye, is also used (Seligman, P. A. et al, 1983 *Am. J Hematol* 14: 57-66; U.S. Pat. No. 6,060, 322). These methods, although useful for measuring mature platelets and reticulated platelets, suffer from certain drawbacks. These methods use size (log forward scatter) and granularity (log side scatter) to identify and resolve the platelets from the rest of the blood components. The broad nature of the metachromatic dye's fluorescence emission precluded the use of fluorochrome conjugated antibodies to identify the platelets.

In blood samples from healthy volunteers, the use of size and granularity is sufficient to include only platelets in the measurement. However, samples from patients with certain diseases have contaminating red cell fragments that fall within the platelet population, causing the platelet area to have an apparent increase in the number of platelets therefore leading to a lower percentage of reticulated platelets. Additionally, where giant platelets, platelet clumps or platelet satellites are present due to a platelet related deficiency or abnormality, the resulting identification or population or quantification can be incorrectly determined by the flow cytometer.

Another compounding issue in conventional flow cytometry measurement methods using nucleic acid dyes is the low platelet count in blood samples obtained from some patients. One example is the disorder called idiopathic thrombocytopenic purpura, in which the patients' own platelets are coated with an autoantibody and removed by the mononuclear phagocyte system. In order to count enough platelets for a statistically valid reticulated platelet percentage in this disease, one must acquire a huge data file with the bulk of the counts still being that of red blood cells.

Such automated flow cytometric methods have also employed platelet-specific antibodies in conjunction with non-metachromatic nucleic acid dyes for the purpose of measuring reticulated platelets. See, for example, Bonan et al 1993 *Cytometry*, 14:690-694; Matic et al 1998 *Cytometry*, 34:229-234; Rinder et al 1998, *Blood*, 91:1288-1294; Robinson et al, 1998, cited above; Balduini, C. L., et al, 1999 *Brit J Haematol* 106: 202-207; Stohlawetz, P., et al 1999 *Thromb Haemost* 81: 613-617; Saxonhouse, M. A. et al, 2004 *J Pediatr Hematol Oncol:* 26, 797-802; Chaoui, D. et al., 2005 *Transfusion:* 45, 766-772). As an example, fluorochrome conjugated antibodies with peak emissions beyond 560 nm are used in conjunction with the dye thiazole orange (TO), which binds to RNA on excitation with a 488 nm laser and has detectable emission from 500 to 560 nm, by using appropriate optical filter and applying fluorescence compensation (Saxonhouse et al 2004, cited above). However, other dyes do not work in this method. For example, the metachromatic dye AO, when bound to RNA, has a broad overlapping emission from 500 nm to 700 nm with the peak around 630 to 670 nm. It is therefore difficult to use AO with fluorochrome conjugated antibodies with emission spectra that span that range, even if fluorescence compensation is also used (Shapiro, H. M. 2003 *Nucleic Acid Dyes and their Uses. In Practical Flow Cytometry*, 4$^{th}$ Edition, H M Shapiro (Ed), John Wiley & Sons, Hoboken, N.J., pp 306-326).

In general, such flow cytometric methods involve lengthy incubation times; and thus such methods are not amenable for use on high throughput hematology systems. This is exemplified in the measurement of reticulated platelets in whole blood with TO and a platelet specific antibody. An anti-CD41 platelet specific antibody was reported in one publication using an incubation time of 15 minutes (Chaoui et al 2005, cited above). The same reagents were used in other methods, but with different incubation times of 30 and 45 minutes respectively (Stohlawetz et al 1999 and Saxonhouse et al, 2004, both cited above). Additional publications using TO and fluorochrome conjugated anti-platelet antibody use incubation times for the antibodies to bind to platelets ranging from 10 to 45 minutes (Bonan et al 1993, Matic et a 1998, Rinder et al 1998, Robinson et al, 1998, Balduini et al 1999, all cited above). These tong incubation times render these assays useless for high throughput hematology systems.

Similarly, in the wider area of nucleic acid dye binding and surface staining with antibodies for blood components other than platelets, the incubation times are similarly long, e.g., 30 minutes (U.S. Pat. No. 5,047,321); and 15 minutes (U.S. Pat. No. 6,287,791) and thus not suitable for automated cell analysis.

There remains a need in the art for rapid analytic methods that enhance the specific identification of platelets and reticulated platelets in clinical situations where low platelet counts or interfering conditions can lead to inaccuracies of the measurement. There also remains a need for such methods that are suitable for performance in an automated hematology analyzer without compromising the throughput of the instrument.

SUMMARY OF THE INVENTION

The methods described herein address the needs in the art by providing various embodiments of methods for platelet hematology analysis which use unique combinations of labeled antibodies that bind to platelets and/or nucleic acid dyes that permit a rapid analysis which includes a short incubation time of less than 5 minutes for substantially simultaneous staining and antibody-binding of platelets. In one embodiment, the rapid method involves an incubation and staining procedure which may be performed in less than 1 minute. In another embodiment, that process is performed in less than 30 seconds.

As one aspect, a method for identifying a platelet population in a biological sample includes incubating for less than 5 minutes the biological sample with at least one labeled, ligand that binds to epitopes and antigens on a platelet population and a nucleic acid dye under conditions in which cells in the sample are permeant to the dye. The incubated sample is passed through a sensing region of a flow cytometer, where it is irradiated with a laser light source. In one embodiment, at least two parameters, e.g., light scatter, direct current, axial light loss, opacity, radio frequency, and fluorescence, are measured. Data produced by these measurements is analyzed, generally by use of two parameters, and one or more platelet populations in the sample are distinguished from other cells.

In yet a further aspect or embodiment, a method for identifying a population of the immature, reticulated platelets in a biological sample comprises incubating for less than 5 minutes the biological sample with a nucleic acid dye and at least one labeled anti-platelet ligand that binds to an epitope on a platelet, wherein the label on the ligand and nucleic acid dye emit fluorescence. The incubated sample is passed through a sensing region of a flow cytometer, wherein said incubated sample is irradiated with a laser light source, and the labeled ligand fluorescence and the nucleic acid dye fluorescence and optionally at least one other parameter selected independently from the group consisting of light scatter, direct current, axial light loss, opacity, radio frequency, and fluorescence are measured. The platelet population in said sample is differentiated or identified by identifying the population of platelets using the data generated by measurements of labeled ligand fluorescence and an additional parameter. Gating on that identified population and then analyzing the measurements produced using the nucleic acid dye fluorescence and an additional parameter allows identification or quantification of the immature, reticulated platelet population.

In yet a further aspect or embodiment, a method using the above-described assay permits diagnosis and monitoring of the progression of platelet-related diseases by identifying or measuring in a biological sample from a mammalian subject certain platelet populations.

Other aspects and advantages of various embodiments of the claims are disclosed in the following detailed description thereof.

BRIEF DESCRIPTION OF THE DRAWINGS

FIG. 1A is a histogram using size/forward scatter (FS) vs. granularity/side scatter (SS), a prior art gating strategy for identifying and enumerating platelets. The cells in this sample were stained with the metachromatic dye Acridine Orange (AO), but not with an anti-platelet antibody. This histogram shows the separation of the platelets (P), red blood cells (RBC) and white cells (WBC) based on size (FS) and granularity (SS). The platelets are the lowest population (P) with an oblong shape.

FIG. 1B displays the same FS vs. SS light scatter gating strategy employed on a sample prepared using the rapid antibody staining method as described herein with a PECy7 fluorescent-labeled anti-CD41 anti-platelet antibody and AO. The separation of the platelets (P), RBCs and WBCs based on size (FS) and granularity (SS) are indicated similarly to the sample of FIG. 1A.

FIG. 1C displays size (FS) and anti-platelet fluorescence (PC7) of the platelet population from the sample of FIG. 1A in which no fluorescent anti-platelet antibody was used. In this case, the platelets are not stained with an anti-platelet antibody and therefore the contoured area (S) is devoid of any platelets, i.e., no fluorescence is detected.

FIG. 1D displays a similar FS v. anti-platelet fluorescence analysis to that shown in FIG. 1C; however, this sample was the same specimen prepared for FIG. 1B. In this specimen, the rapid antibody staining method was employed using PECy7 fluorescent-labeled anti-CD41 anti-platelet antibody that emits in the 760-820 nm range and AO. This histogram displays the size and fluorescence of the platelet population in which the platelets are bound with CD41-PECy7 anti-platelet antibody. The platelets in this histogram appear as a distinct fluorescent population (S). Particles that are not platelets are non-fluorescent and appear to the left of the fluorescent platelets as events along the Y-axis, i.e., debris (D).

FIG. 1E displays FS vs. nucleic acid dye fluorescence of the same blood specimen as described in FIGS. 1A and 1C. This histogram shows the size and fluorescence of red blood cells, white blood cells, and platelets including reticulated platelets. The platelets appear as an arc and are well separated from the rest of the cells. The red cells have lower fluorescence than platelets. The white cells, having DNA, are off scale and seen as vertical lines (WBC) on the top right hand corner of the histogram. The reticulated platelets, as indicated, are the brighter fluorescent population in the platelet population.

FIG. 1F displays FS vs. nucleic acid dye fluorescence of platelet population identified in the histogram of FIG. 1D. Because this histogram gates on the pure population of platelets devoid of debris and other cells that had been identified and resolved by anti-platelet antibody staining (FIG. 1D), it allows for accurate enumeration of platelets and reticulated platelets. The reticulated platelets, which are the immature platelets, are larger in size as demonstrated by forward scatter and brighter in AO fluorescence due to the presence of platelet reticulum or granules.

FIG. 2A is a histogram that analyzes the sample using light scatter only, i.e., forward scatter (FS) vs. side scatter (SS). The platelets are identified by the region labeled P.

FIG. 2B is a histogram that analyzes the same sample using FS vs. anti-platelet antibody fluorescence. This histogram demonstrates the separation of the stained platelets (S) from the debris (D)) and other cells with anti-CD41 PECy7 fluorescence.

FIG. 2C analyses the platelet population using FS vs. AO fluorescence by gating on the platelet population identified in FIG. 2A. This resulting histogram shows a region of debris (D). The use of size (FS) and granularity (SS) as in FIG. 2A includes debris in the calculation leading to lower percentage of reticulated platelets, i.e., 16.6%, which is a limitation to the use of only light scatter for platelet population analysis.

FIG. 2D analyzes using FS vs. AO fluorescence the pure platelet population apart from debris as previously identified as "S", in the histogram of FIG. 2B. The FS and anti-platelet fluorescence region of FIG. 2B excludes the debris (D). The histogram of FIG. 2D thus provides improved resolution of platelets and a higher percentage of reticulated platelets, i.e., 22.6%.

FIG. 3A is a histogram displaying forward scatter (FS) vs. side scatter (SS) and shows the separation of platelets and RBCs by use of light scatter parameters only.

FIG. 3B displays FS vs. anti-platelet antibody fluorescence of the platelet population for the same patient sample used in FIG. 3A. The platelets in FIG. 3B were bound with anti-CD41 PECy7. This histogram demonstrates the separation of the platelets from the debris and other cells with anti-CD41 PECy7 fluorescence.

FIG. 3C displays FS vs. AO fluorescence analysis of the platelet population identified in FIG. 3A by light scatter only, leading to an estimate of the reticulated platelet population of 23.0%.

FIG. 3D, in contrast to FIG. 3C, displays FS vs. AO fluorescence of the pure population of stained platelets identified in FIG. 3B by antibody staining. The population of FIG. 3B evaluated by FS vs. AO fluorescence provides a more accurate, higher percentage of reticulated platelets, i.e., 25.4%, for the same patient sample.

FIG. 4A displays forward scatter (FS) vs. side scatter (SS) for a sample prepared without any antibody for resolving and enumerating platelets. Separation of the platelets (P), red blood cells (RBC) and white cells (WBC) in a healthy volunteer sample are shown based on size (FS) and granularity (SS). The platelets are the lowest population (P) with an oblong shape.

FIG. 4B displays FS vs. PC7 fluorescence for a sample in which a fluorescent antibody with no specificity for platelets was mixed with the sample. Because the platelets were not stained, the contoured area (S) is devoid of any platelets. No platelet population was identified by use of the two parameters.

FIG. 4C displays FS vs. anti-platelet (PC7) fluorescence on a sample prepared using the rapid staining method with PECy7 fluorescent-labeled anti-CD41 anti-platelet antibodies that emit in the 760-820 nm range and AO. The platelets in this histogram appear as a distinct fluorescent population. Particles that are not platelets are non-fluorescent and appear to the left of the fluorescent platelets as events along the Y-axis (D). This area is increased in events when a patient sample stained with the antibody is measured.

FIG. 4D illustrates FS vs. AO fluorescence of the platelet population of the subject in which the sample was stained with AO, and no antibody. This platelet population was identified in FIG. 4A by light scatter only. The platelets appear as an arc and are well separated from the rest of the cells. The red cells and white cells are not visible because the plot is based (gated) on the platelet population from FIG. 4A. The reticulated platelets, as indicated, are the brighter fluorescence in the platelet population.

FIG. 4E displays FS vs. AO fluorescence analysis of the platelet population of the sample of FIG. 4B, which sample lacks staining by the non-specific antibody. The histogram of FIG. 4E therefore shows no AO fluorescence because the histogram of FIG. 4B did not identify a platelet population.

FIG. 4F displays FS vs. AO fluorescence of the sample stained with PECy7 fluorescent-labeled anti-CD41 anti-platelet antibodies and with AO, and isolated as described in FIG. 4C. Because the platelet population was identified and resolved by anti-platelet antibody staining in FIG. 4C, it allows for accurate enumeration of reticulated platelets by relating to the pure platelet population. The reticulated platelets measured in the absence (16.4%, FIG. 4D) and presence (22.1%, FIG. 4F) of anti-platelet specific antibody are similar in a healthy volunteer sample. However, the population is more accurately identified and higher than that of FIG. 4D.

FIGS. 5A-5F are two parameter histograms from samples obtained from a patient having mild thrombocytopenia. All samples were prepared according to the rapid staining method with at least one anti-platelet antibody (anti-CD41 and/or anti-CD61) and the nucleic acid dye, AO.

FIG. 5A displays the parameters of forward scatter (FS) vs. anti-platelet fluorescence of a sample stained with PECy7 fluorescent-labeled anti-CD41 anti-platelet antibodies and AO.

FIG. 5B is a similar analysis, but of a sample stained with PECy7 fluorescent-labeled anti-CD61 anti-platelet antibodies and AO.

FIG. 5C is a similar analysis, but of a sample stained with PECy7 fluorescent-labeled anti-CD41 anti-platelet antibodies and PECy7 fluorescent-labeled anti-CD61 anti-platelet antibodies and AO.

FIG. 5D is a histogram that displays the parameters of FS vs. AO fluorescence gating on the platelet population identified in FIG. 5A, showing 21.5% reticulated platelets.

FIG. 5E displays FS vs. AO fluorescence analysis of the platelet population identified in FIG. 5B, showing 21.9% reticulated platelets.

FIG. 5F displays FS vs. AO fluorescence analysis of the platelet population identified using the two anti-platelet antibodies of FIG. 5C, showing 23.5% reticulated platelets.

DETAILED DESCRIPTION OF THE INVENTION

Figure 1A:
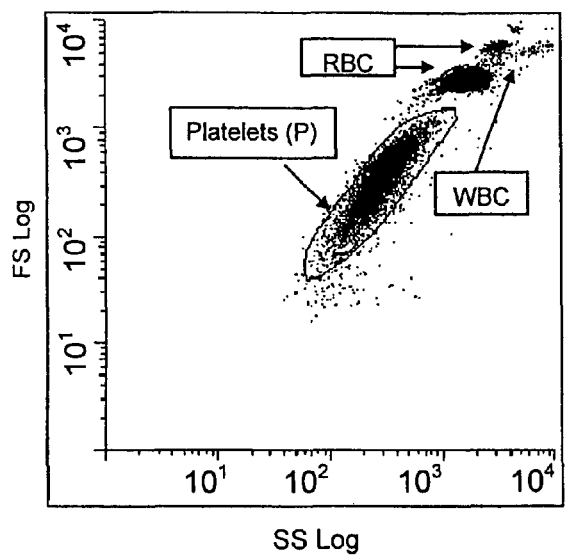
FIGS. 1A-1F are two parameter histograms of samples from a healthy patient whose blood specimen was prepared for analysis by staining with a nucleic acid dye, Acridine Orange, and no antibody (1A, 1C and 1E) or whose blood specimen was prepared by admixture and incubation with an anti-platelet antibody and AO (1B, 1D and 1F), as described herein.

The method described herein permits the automated and rapid analysis and identification of one or more platelet populations in a biological sample. This method enhances the specific identification and/or quantification of total platelet populations and subsets of platelets in clinical situations where either low platelet counts or interfering conditions can lead to inaccuracies of the measurement. In addition, this assay method employs rapid staining that allows for incorporation of this method into an automated hematology analyzer without compromising the throughput of the instrument. This method achieves its advantages over current platelet identification assays in the art through combinations of labeled anti-platelet ligands and nucleic acid dyes that permit rapid staining of the platelets and other cells in the sample. This method is designed for hematological analysis that identifies a maximal number of platelet populations and/or allows separation of the platelet population from other cells more accurately, while using a minimal number of assay components. In one embodiment, this method permits rapid and accurate identification of a population of immature, reticulated platelets in a sample.

As used herein "platelet population" includes the individual platelet subpopulations such as the mature platelet population, the immature reticulated platelet population, the giant platelet population, a population of platelet clumps, and a population of platelet satellites. Total mature platelets including activated platelets and resting (non-activated) platelets are identified. In one embodiment, a total platelet population consisting of all of the above platelet subpopulations is identified and/or measured. The method may also be employed to identify populations of two or more of the above-noted platelet subpopulations.

This assay method involves a rapid incubation of the biological sample with at least one labeled, anti-platelet ligand or platelet-specific ligand and a nucleic acid dye under conditions in which cells in the sample are permeant to the dye. The resulting incubated sample is exposed to a light laser and parameter data is collected. The differentiation of platelet populations is thereafter based upon the combination and evaluation of the parameter measurements, including e.g., anti-platelet fluorescence and fluorescence of the nucleic acid dye.

A. Rapid Incubation

1. The Biological Sample

The "biological sample" includes any mammalian cell-containing suspension that contains platelets. Such a specimen or sample can include hematological cells and non-hematological cells. Exemplary samples include whole blood, peripheral blood, plasma, and platelet-rich plasma. Such a sample includes, without limitation, whole blood, peripheral blood, plasma, platelet-rich plasma, bone marrow aspirate, lymph node tissue, splenic tissue, cerebrospinal fluid, skin tissue, mucosal tissue, thoracentesis fluids, pleural fluids, and spinal fluid. However, any suspension, tissue or fluid that contains a platelet population for analysis may be employed in this assay. Hematological (i.e., blood) cell populations include mature and immature, variant and atypical white blood cells and red blood cells, reticulated red blood cells, nucleated red blood cells, various platelet populations, reticulated platelets and megakaryocytes. In the blood, atypical cells include various forms of myelocytes, immature granulocytes, band cells, blast cells, atypical lymphocytes, variant lymphocytes, nucleated red blood cells, giant platelets, platelet clumps and platelet satellites, etc. In one embodiment, the nucleated cell populations comprise nucleated red blood cells and leukocytes. Non-hematological cells include epithelial cells and endothelial cells, among others. The sample may optionally also contain cellular debris and non-cellular aggregates.

Preferably, the biological sample is human whole blood or peripheral blood or plasma or plasma-rich sample which is normal or which contains atypical cell populations due to disease, reaction to an adverse environmental stimulus, e.g., a carcinogen, or as a result of therapeutic treatment. The method described herein may also be employed in analysis of samples from other mammals including, without limitation, domestic animals, such as dogs and cats, and larger mammals, such as farm animals or horses, among others.

In one embodiment, the sample contains cells that are naturally permeant to the nucleic acid dye used in the method. Alternatively for performance of the method, cells in the sample are rendered permeant to the dye during sample preparation preceding performance of the assay, as described below. In other embodiments, the sample contains lysed cells.

In one embodiment, the sample may also contain other components, such as buffers. Suitable buffers include those that maintain the pH of the sample during the incubation and parameter measurement in the range of about 6 to about 9. Desirably, a pH in the range of about 7 to about 7.5 is maintained in the sample. Additionally, such buffers may also be used to adjust the concentration of one or more of the ligand or dye components of the method. Examples of buffers that can be utilized in the methods described herein include, without limitation, phosphate buffered saline or isotonic saline, such as ISOTON II, Coulter Corporation, Miami, Fla., or the like. See, U.S. Pat. No. 3,962,125, which is hereby incorporated by reference. Selection of an appropriate buffer is not a limitation of the rapid staining method.

For use in this rapid-staining method, the biological sample volumes can be altered to fit the requirements of the system, but preferably range from about 10 μL to about 150 μL. More particularly, the sample volume can be at least about 20, 30, 40, 50, 60, 70, 80, 90, 100, 110, 120, 130 or 140 μL.

2. The Ligand

The term "ligand" as used herein refers generally to a protein, peptide or nucleic acid sequence that binds designated targets, e.g., an epitope, antigen or receptor, present on platelet populations. In certain embodiments, a ligand is a highly specific polyclonal, monoclonal, synthetic or recombinant antibody of classes IgG, IgM, IgA, IgD and IgE, a chimeric antibody formed by the combination of two types or species of antibody, and a humanized antibody containing another species antibody variable regions within a human antibody backbone. All such antibodies are directed to an epitope or antigen or cell surface receptor expressed on a platelet. In another embodiment, a useful ligand useful in this assay can also be an antibody fragment, such as a Fab fragment, a Fab' fragment, a F(ab')$^2$ fragment, an fd fragment, or an Fc antibody fragment, of one of the above types of antibody. In other embodiments, a ligand is a single chain variable antibody fragment. Still another suitable ligand is a recombinant construct comprising a complementarity determining region (CDR) or a construct which shares sufficient CDRs to retain functionally equivalent binding characteristics of an antibody that binds the targeted epitope or antigen that is expressed on a platelet population.

The term "platelet-specific ligand" used in this assay in one embodiment is a ligand that specifically binds to an epitope, antigen or receptor that is expressed exclusively on a platelet population or is expressed differentially on different platelet populations. An epitope, antigen or receptor exclusively expressed on platelets is not expressed on red blood cells, white blood cells, epithelial cells or endothelial cells. For example, among exclusively platelet-expressed epitopes or antigens or receptors are the proteins designated CD41 (GPIIb), CD61 (GPIIIa), CD42b (GPIb), CD42a (GPIX), CD42d (GPV), CD42bCD42a (GP1bIX), CD42bCD42aCD42d (GP1b-IX-V), CD41CD61 (GPIIIb-IIIa), and CD62p (P-selectin/GMP-140), which are known to characterize platelet populations only. Thus an example of a platelet-specific ligand of this type is an anti-GP1b monoclonal antibody, an anti-GPIX monoclonal antibody, an anti-GP1bIX monoclonal antibody, an anti-GPIIb-IIIa monoclonal antibody, an anti-GPIV monoclonal antibody, or an anti-GMP-140 monoclonal antibody or a portion thereof. The platelet-specific epitope or antigen also includes fragments of the above-identified antigens. The platelet-specific epitope or antigen as defined above also includes those antigens which are expressed only on certain subsets of platelets, or are expressed differentially on certain subsets of platelets. For example, CD62p is a receptor which is expressed in higher density on activated platelets than on resting platelets, and thus an anti-CD62p may be employed to distinguish between these two subsets of platelets in the methods described herein.

The term "anti-platelet ligand" refers to a ligand that binds to an epitope, antigen or receptor that is expressed, or differentially expressed, on platelets and on at least one additional cell population. Certain epitopes may be expressed differentially on platelets and also differentially expressed on two or more additional cell populations, so that a ligand binding such epitopes may be used to identify multiple cell types using various parameters for identification as described below. For example, the additional cell population can be selected from red blood cells, white blood cells, epithelial cells or endothelial cells. In one embodiment, an epitope or antigen that is expressed or differentially expressed on platelets and on red blood cells includes, without limitation, the following epitopes, antigens or fragments thereof: CD36, CD47, CD55, CD58, CD99, CD111 and CD147. Thus, suitable anti-platelet ligands of this type for use in the method include an anti-CD36 antibody, anti-CD47 antibody, anti-CD55 antibody, anti-CD58 antibody, anti-CD99 antibody, an anti-CD111 antibody, and an anti-CD147 antibody, among others, or a portion thereof.

In another embodiment, an epitope or antigen that is expressed on platelets and on white blood cells includes, without limitation, the following epitopes, antigens or fragments thereof: CD9, CD17, CD31, CDw32, CD36, CD49, CD51, CDw60, CD84, CD114, and CD151. Thus, a differentially expressed anti-platelet ligand of this type is, e.g., an anti-CD84 antibody, an anti-CDw32 antibody or anti-CD49 antibody or a portion thereof.

In still another embodiment, an epitope or antigen that is expressed on platelets and on epithelial cells includes, without limitation, the following epitopes, antigens or fragments thereof: CD9, CDw17, CD29, CD46, CD47, CD49b, CD55, CD60b, CD82, CD98, CD99, CD110, CD111, CD112, CD151 and CD165. Thus, a differentially expressed anti-platelet ligand of this type is, e.g., an anti-CDw17 antibody, an anti-CD112 antibody or anti-CD49b antibody or a portion thereof.

In a further embodiment, an epitope or antigen that is expressed on platelets and on endothelial cells includes, without limitation, the following epitopes, antigens or fragments thereof: CD31, CD114, CD 151 and PECAM-1. Thus a differentially expressed anti-platelet ligand of this type is an anti-PECAM-1 antibody, anti-CD31 antibody, anti-CD114 antibody or an anti-CD151 antibody or portion thereof.

In one embodiment, the method employs one platelet-specific ligand or one anti-platelet ligand. In another embodiment, the method employs two or more different platelet-specific ligands. In another embodiment, the method employs two or more different anti-platelet ligands. In still another embodiment, the method employs a platelet-specific ligand and an anti-platelet ligand that bind different determinants on a platelet. In another embodiment, such ligands (or combination of ligands) are capable of differentiating between mature platelets and immature platelets, based on differential expression of the antigenic determinant on platelets as they mature and age. The individual ligand/antibody specificities in conjunction with each other as well as the additional measured parameters are able to provide the most information in a single analysis. The use of various combinations of these ligands/antibodies which bind antigenic determinants on platelets only or on platelets and other blood cells permits further identification and distinction among the normal and atypical cell types.

The ligand selected for use in the various embodiments of this method is typically labeled with a detectable label, as defined below. Optimal concentrations of ligands/antibodies used in the method are defined based upon label selected, desired staining intensity, reaction kinetics and fluorescence carryover between fluorescence channels when using multiple antibodies with only one or two fluorochrome labels. Such concentrations may be determined by the person of skill in the art given the present teachings.

Desirably, the ligands/antibodies are designed for admixture into a single reaction mixture with a biological sample.

3. Labels

Each ligand or antibody used in this rapid staining method is associated or coupled with a selected detectable label. In one embodiment, the label is a fluorescent label. In another embodiment, the label is a non-fluorescent label. In embodiments, in which multiple labeled ligands are used, a combination of both fluorescent and non-fluorescent labels is employed. Such labels include, without limitation, fluorochromes, fluorescent and non-fluorescent beads fluorescent or non-fluorescent colloidal particles, quantum dots, and fluorescent resonance energy transfer (FRET) labels.

In one embodiment, the detectable label is a fluorescent label, i.e., a fluorochrome commonly used in diagnostic assays. Commonly used fluorochromes useful in labeling ligands/antibodies include the blue excitable fluorochromes, such as fluorescein isothiocyanate (FITC), Alexa 488, phycoerythrin (PE), PE-cyanin-5 (PCS), PE-cyanin-7 (PC7), PE-Texas Red (ECD) and Peridinin-chlorophyll-protein (PerCP) and the red excitable fluorochromes such as allophycocyanin (APC), Alexa 647, and APC-Cy7. Still other useful fluorochromes include the tandem dyes, e.g., PE-cyanin-5.5, PE-Cy7, PE-Alexa750, and rhodamine. Alexa dyes, which are not tandem dyes, are also useful. Combinations of such labels, such as Texas Red and rhodamine, FITC+PE, FITC+PECy5, and PE+PECy7, among others may be used depending upon the type of laser employed in the flow cytometry apparatus. Other fluorochromes may be employed in the method, and may include those excitable by radiation in the red, blue, violet or green wavelengths or combinations thereof. Multiple fluorochromes may be independently selected from available fluorochromes.

Alternatively, indirect labeling methods, such as biotin-avidin or primary and secondary labeled antibodies are useful to accomplish a similar effect.

All of these fluorescent labels are commercially available, and their uses known to the art. Still other fluorescent labels may be available from other sources or may be developed in the future. Such fluorescent dyes or fluorochromes are anticipated to be useful in the method in the same manner as is the exemplary fluorescent label of the examples below.

Each fluorochrome has a characteristic "emission spectrum", of which a portion is a characteristic "peak emission spectrum". As used herein the term "emission spectrum" means generally the amount of electromagnetic radiation of each frequency a fluorochrome emits when it is excited. Generally, an emission spectrum is a range or profile formed by bands of certain frequency, usually measured in nanometers (i.e., wavelength). As used herein, the term "peak emission spectrum" means the most intense portion of the emission spectrum usually measured as maximum wavelength in nanometers. The peak emission spectrum for any given fluorochrome (and for most nucleic acid dyes with narrow emission spectra) is known and readily obtained from publications describing such fluorochromes, such as Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995) Molecular Probes, and other similar texts or corresponding website, known to those of skill in the art and incorporated herein by reference. The peak emission spectrum for any given fluorochrome may also be obtained by performing a spectral scan using a spectrophotometer. Thus, in certain embodiments, labels on ligands used in this method may having overlapping peak emission spectra with other fluorochrome labels and/or with the nucleic acid dye used in the method.

Methods for coupling or associating the label with the ligand, e.g., antibody, are similarly conventional and known to those of skill in the art. Known methods of label attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995); U.S. Pat. Nos. 6,692,968 and 5,164,311, among others. Thus, selection of the coupling methods does not limit this invention.

According to various embodiments of the method, one fluorochrome is used to label a single ligand employed. Alternatively, the same or different fluorochromes are employed to label multiple ligands (e.g., antibody or antibodies) used in the method. The identity of the fluorochromes selected as a label depends upon whether the same fluorochrome or different fluorochromes are used to label two or more antibodies in the composition. If the same fluorochrome is used to label more than one antibody, each antibody will have "overlapping peak emission spectra". Such an overlap between identical fluorochromes is non-compensatable or non-separable. If two or more fluorochromes are used, one may select different fluorochromes, each with different peak emission spectra, which may be optionally overlapping peak emission spectra. In an embodiment, the peak emission spectra of the fluorochrome label on one antibody in the method may overlap the peak emission spectra of the fluorochrome used to label another antibody to form a non-compensatable spectral emission.

By the phrases "non-compensatable", "non-resolvable" or "non-separable" as applied to the spectral pattern formed by the overlapping emission spectra is meant that the spectral pattern formed by the overlap of the peak emission spectra of the fluorochromes labeling two antibodies cannot be separated or resolved into the component peak emission spectra. In one embodiment, the overlapping spectral pattern is not separable by current optics or color compensation methods (optical or electronic). Thus, the resulting non-compensatable spectral pattern is different from either of its component fluorochrome peak emission spectra and can be employed in analysis methods with the different cellular specificities of the antibodies and/or dyes used in a composition, to create a histogram that identifies different platelet or other blood cell subsets or populations. Suitable pairs of fluorochromes that form non-compensatable overlapping spectral emission patterns include, without limitation, the blue excitable pairs: FITC and Alexa 488, PE and Cy3, PC5 and PeCy5, PC5 and PerCP, PeCy5 and PerCP, PC7 and PeCy7, and the red excitable pair: APC and Alexa 647. Where two lasers of different color are used in the fluorescent analysis, suitable fluorochrome pairs include, without limitation, PC7 and APC-Cy7, and PeCy7 and APC-Cy7.

Alternatively, one may use different fluorochrome pairs which do not have overlapping peak emission spectra (referred to hereinafter as "non-overlapping" fluorochromes). For example, selected coupled fluorochromes for use (using one or two lasers) include PE (peak emission spectrum~575 nm)+PECy5 (peak emission spectrum~670 nm), PE+APC (peak emission spectrum~660 nm), FITC (peak emission spectrum~520 nm)+PE, APC+PECy7 (peak emission spectrum~770 nm), and PE+PECy7. All of these pairs of fluorochromes have non-overlapping peak emission spectra. These lists of fluorochrome pairs that have non-compensatable overlapping emission spectra or compensatable overlapping emission spectra or emission spectra that do not overlap are representative only and do not attempt to include an exhaustive list. One of skill in the art should be readily able to select the appropriate fluorochrome combinations for use in the methods described herein in view of the additional teachings of this specification.

In one embodiment of the rapid staining method, the label conjugated to the above-noted ligand(s) is a fluorescent label that has an emission spectrum that is distinguishable from that of the nucleic acid dye employed in the method. In another embodiment, the platelet-specific or anti-platelet ligand is labeled with a fluorescent label that has an emission spectrum that overlaps with that of the nucleic acid dye. In the latter embodiment, such overlapping emission spectra may or may not be compensatable or resolvable at the peak emission spectrum of at least one of the fluorescent labels or the nucleic acid dye used in the method.

Still other non-fluorescent labels may be employed in this rapid staining method. For example, the antibodies may be labeled with e.g., radioactive compounds, chemiluminescent labels or proteins, such as biotin, or enzymes, or molecular labels such as FLAG, etc. See, e.g., Chubet R G, Brizzard B L. 1996 Biotechniques 20(1):136-141; and Knappik A, Pluckthun A. 1994 Biotechniques 1994; 17(4):754-761. Other elements of the detectable labels include substrates useful for generating the signals upon interaction with the other components, e.g., a streptavidin and horseradish peroxidase system. Suitable labels are selected from among a wide array of conventionally employed detectable diagnostic labels.

In one desirable embodiment, the fluorochrome used in the methods described herein is PE-Cy7.

4. Nucleic Acid Dyes

The rapid staining method described herein takes advantage of nucleic acid dyes which can permeate the cells in the sample and stain the nucleic acid rapidly, as defined below. Nucleic acid specific dyes emit fluorescence of a certain wavelength based on their RNA or DNA bin ding capacity (Darzynkiewicz, Z and Kapuscinski J 1990 "Acridine Orange: A versatile probe of nucleic acids and other cell constituents." In Flow Cytometry and Sorting, $2^{nd}$ Edition, M R Melamed, T Lindmo and M L Mendelsohn (Ed), Wiley-Liss Inc, New York, pp 291-314).

With reference to the fluorescent dyes useful in this invention, the term "emission spectrum" is defined in the same way as defined for fluorochromes above. Some dyes have broad emission spectra with a broad "peak" that extends for more than 200 nm. Other dyes have narrow peak emission spectra. Emission spectra for such dyes are also known in the art and published in a variety of well-known texts. See, e.g., Darzynkiewicz, Z and Kapuscinski J (1990). Acridine Orange: A versatile probe of nucleic acids and other cell constituents. In Flow Cytometry and Sorting, 2nd Edition, M R Melamed et al (Ed), Wiley-Liss Inc, New York, pp 291-314. Shapiro, Howard M. (2003) Practical Flow Cytometry $4^{th}$ edition, Wiley-Liss, Hoboken, N.J. pp. 296-297. Invitrogen website: www.Invitrogen.com.

The fluorescent dye is, in one embodiment, a nucleic acid dye. In another embodiment, the fluorescent dye is a cytophilic dye. In one embodiment, the nucleic acid or dye is a cell-permeant dye. The dye may be metachromatic or non-metachromatic, or cell permeant or non-cell permeant. By the term "cell permeant" is meant to describe a dye that readily penetrates a cell membrane and stains the components of the cell without requiring the additional presence of a permeabilizing agent in the composition or reaction mixture. Typically, cell-permeant dyes are utilized to stain live cells or components of cells that have not been lysed.

In another embodiment, the fluorescent dye is a cell-impermeant dye, such as those cell-impermeant dyes within the red, green, violet or blue-excited wavelength regions. Use of this dye in an embodiment of the method is generally accompanied by pre-treatment of the sample to lyse the cells, as provided below.

In a further embodiment, the fluorescent dye is an intercalating dye and/or a metachromatic dye. See, for example, the metachromatic dyes noted in Urban et al., 2000 Acta. Histochem. 102:259-272.

In a further embodiment, the fluorescent dye is a non-metachromatic dye. The term "non-metachromatic dye" is meant to describe a fluorescent dye that provides a single wavelength of excitation and/or emission when irradiated at a predetermined wavelength.

Fluorescent dyes useful in various aspects may share a combination of the above characteristics. For example, in one embodiment of this method, the nucleic acid dye is Acridine Orange, a blue excitable, nucleic acid dye, which is metachromatic and cell permeant. Another useful dye is propidium iodide, which is a blue excitable, nucleic acid dye which is non-metachromatic and non-cell permeant. Another useful dye is Thiazole Orange, which is a non-metachromatic, cell permeant nucleic acid dye which excites in the blue 488 nm wavelength. Fluorescein diacetate is another blue excitable dye which is not a nucleic acid dye, but a non-metachromatic, cell permeant, enzyme substrate dye. Rhodamine 123 is a blue-excitable, non-metachromatic cell permeant mitochondrial dye useful in certain embodiments of the method. The red excitable SYTO61 dye is a non-metachromatic, cell permeant, nucleic acid dye that excites at about ~633 nm. Similarly the red excitable dye TO-PRO-3 is a non metachromatic, non-cell permeant, nucleic acid dye useful in certain embodiments of the rapid staining method.

Examples of other fluorescent dyes that may be utilized in the various embodiments of methods described herein include, without limitation, the Pyronin Y dye, acridine dyes, the nonyl Acridine Orange dye (3,6-Bis-(dimethylamino)-10-nonylacridinium bromide, Molecular Probes, Eugene, Oreg.), and the Acridine Red dye (also commercially available as Pyronin B, Sigma-Aldrich Corp., St. Louis, Mo.); the Thiazole Orange dye (Becton Dickinson, Franklin Lakes, N.J.); Propidium Iodide (3,8-Diamino-5-(3-diethylaminopropyl)-6-phenyl-phenanthridinium diiodide, Sigma-Aldrich Corp., St. Louis, Mo.); Ethidium Bromide (Sigma-Aldrich Corp., St. Louis, Mo.); Hexidium Iodide (Molecular Probes, Eugene, Oreg.); Dihydroethidium (Molecular Probes, Eugene, Oreg.); Ethidium Monoazide (Molecular Probes, Eugene, Oreg.), the Toluidine Blue dye (2-Amino-7-dimethylamino-3-methylphenothiazinium chloride, Sigma-Aldrich Corp., St. Louis, Mo.); the TOPRO-3 dye; the YOPRO-1 dye; the SYTO™ dye such as the SYTO™ 17 dye and the SYTO™ 59 dye through SYTO™ 64 dye; the TOTO™ dye such as the TOTO-1 dye and the TOTO-3 dye; the PO-PRO-3 dye; the YOYO™ dye such as the YOYO-1 dye; the BOBO™ dye; the POPO™ dye such as the POPO-3 dye; xanthene dyes; carbocyanine dyes; polymethine dyes including Astra Violet F R; Thiofalvine T; pseudoisocyanine; oxacarbocyanine dyes; azine dyes; diphenylmethane dyes; methine dyes; oxazine dyes; cyanine dyes; styryl dyes; and hydrosystilbamidine (Molecular Probes, Eugene, Oreg.). Many of these dyes, as well as others that can be utilized in the methods described herein, are commercially available from Molecular Probes Inc. (Eugene, Oreg.). See, U.S. Pat. No. 5,563,070, which is hereby incorporated by reference.

Examples of non-metachromatic dyes include, without limitation, the Neutral Red dye (3-Amino-7-dimethylamino-2-methylphenazine hydrochloride, Sigma-Aldrich Corp., St. Louis, Mo.), the Basic Orange™ 21 dye (Sigma-Aldrich Corp., St. Louis, Mo.), the DiOC dye (1,1'-Dimethyloxacarbocyanine, Molecular Probes, Eugene, Oreg.), the Pyronin™ Y dye (Polysciences, Inc., Warrington, Pa.), the Methylene Blue™ dye (3-Bis-(dimethylamino)-phenothiazin-5-ium chloride, Molecular Probes, Eugene, Oreg.), the Auramine™ O dye (4,4'-(Imidocarbonyl)-bis-(N,N,-dimethylaniline) monohydrochloride, Sigma-Aldrich Corp., St. Louis, Mo.), the LDS™ 751 dye (Quinolinium, 6-(Dimethylamino)-2-[4-[4-(dimethylamino)phenyl)-1,3-butadienyl)-2-ethyl perchlorate, Molecular Probes, Eugene, Oreg.), the Red series dyes, among others, and combinations thereof. See, e.g., various Beckman Coulter catalogs; The Handbook of Fluorescent Probes and Research Products, $6^{th}$ Ed., R. P. Haugland, Molecular Probes, Eugene, Oreg. It should be noted that certain dyes can be metachromatic in some circumstances and non-metachromatic in others.

Examples of metachromatic dyes that can be utilized in the methods and compositions described herein include, without limitation, the xanthene dyes, carbocyanine dyes, polymethine dyes including Astra Violet FR, thiofalvine T, psuedoisocyanine, oxacarbocyanine dyes, acridine dyes, azine dyes, diphenylmethane dyes, methane dyes, oxazine dyes, cyanine dyes, and styryl dyes, among others. See, e.g., the metachromatic dyes noted in Urban et al., 2000 *Acta. Histochem.* 102:259-272.

The recent production of a new tandem dye of fluorochrome(s) that has/have peak emission wavelengths greater than 750nm enables the use of a metachromatic dye with a fluorochrome-conjugated ligand. For example, as demonstrated in the examples below, the use of the nucleic acid dye AO with that tandem fluorochrome PE-Cy7 that is conjugated to the anti-platelet ligand or platelet-specific ligand enables a rapid staining during incubation in this method. The use of this combination is compatible in the platelet arena where there is no platelet DNA to cause significant spillover of the AO bound DNA emission greater than 750 nm.

Thus, in one embodiment of the rapid staining method, the fluorescent dye is Acridine Orange or nonyl Acridine Orange. In another embodiment, the dye is Thiazote Orange. In still another embodiment the dye is Propidium Iodide. In another embodiment, the dye is Acridine Red or Toluidine Blue dye.

In one embodiment the emission spectrum of the fluorescent dye overlaps one or more peak emission spectra of one or more fluorochrome labels used in the method. In another embodiment, the emission spectra of the nucleic acid dye and the label on the ligand are non-overlapping.

In one embodiment of the methods described herein, the nucleic acid dye used is Acridine Orange and the fluorochrome is PECy7. Various combinations of dyes and fluorochromes may be used in the rapid staining method in the same manner as described for the Acridine Orange and PECy7 which are used in the following examples.

5. Incubation Conditions

It is an advantage of this method that the incubation time for contact between the sample, ligand and dye, in one embodiment, is less than about 5 minutes. In one embodiment, the assay incubation time between the sample and the ligand and dye is about 1 minute. In still another embodiment, the incubation time is less than 30 seconds. This method may also be practiced using incubation times of at least 5 seconds, 10 seconds, 15 seconds, 20 seconds, 30 seconds, 40 seconds, 50 seconds, 1 minute, 1.5 minutes, 2 minutes, 2.5 minutes, 3 minutes, 3.5 minutes, 4 minutes, 4.5 minutes or up to 4.9 minutes. Similarly the incubation time can be any fractional portion of time expressed in minutes and seconds up to 5 seconds.

The reaction time for the reaction mixture of about 1 minute is achieved if one adjusts the individual antibody and reagent concentrations, incorporating the use of sphering agents in the formulation and optimizing mixing. This type of rapid reaction time has been demonstrated in the laboratory and is required for an automated high throughput system.

The components of the reaction mixture are allowed to react by incubating at room temperature. Generally ambient temperature is employed, although the temperature is not an issue. In other embodiments, the temperature may vary up to about 37° C., provided that it is sufficient for viability of the cells in the sample.

Another condition of the incubation step of the assay described herein involves the concentration of the ligand and nucleic acid dye reagents used in the methods. In one embodiment, an increase in the concentration of ligand/antibody decreases the incubation time (or increases the reaction kinetics) with the sample. Thus, the greater is the concentration of ligand, the lesser is the incubation time, i.e., the more rapid the assay. In one embodiment, for about 10 to about 200 µL of sample, about 0.1 to about 2 µg of each ligand/antibody is added. In another embodiment the ligand is present in a concentration of between about 0.1 to about 2 µg/100 µL sample.

The concentration and nature of the nucleic acid dye can impact the rapidity of the incubation time. For instance, if the dye is cell permeant, the assay time is reduced. Typically, the concentration of nucleic acid dye in this assay is about 0.3 to about 2.0 µg/ml in the sample. In another embodiment, the nucleic acid dye is in a concentration of about 0.6 µg/ml in the sample. The nucleic acid dye is introduced into the reaction mixture. Lower or higher concentrations are possible if one adjusts the antibody concentrations, blood volumes, incubation and/or mixing times, appropriately. The identity and number of the ligands employed in the method also can impact the rapidity of the method.

In one embodiment of the rapid staining method, to render cells in the sample permeable to the assay reagents, particularly the nucleic acid dye, the sample is contacted with a sphering agent. This contact occurs prior to, or during, incubation with the nucleic acid dye and anti-platelet ligand or platelet-specific ligand. Sphering agents can be readily selected by one of skill in the art. Desirably, the sphering reagent is a zwitterionic surfactant which isovolumetrically spheres the red blood cells and reticulocytes and increases permeability. Such reagents can also act as surfactants. Examples of sphering agents include the non-ionic surfactant Dodecyl-β-D-Maltoside, which suitably is in solution with a buffer such as phosphate buffered saline, zwitterionic agents such as alkyl amido betaine or an alkyl betaine such as lauroamidopropylbetaine, cocoamidopropylbetaine and cocoamidosulfobetaine, N-tetradecyl-N,N-dimethyl-3-ammonio-1-propanesulfonate, or N-dodecyl-N,N-dimethyl-3-ammonio-1-propanesulfonate. See, U.S. Pat. Nos. 5,633,167 and 5,438,003, which are hereby incorporated by reference. To effectively isovolumetrically sphere cells within a blood sample, the concentration of the sphering reagent in the sample is most preferably from about 3 µg/ml to about 50 µg/ml with a mOsm in the range of about 200 to about 400 mOsm, and preferably from about 250 mOsm to about 350 mOsm. However, one of skill in the art may readily adjust this concentration and osmolarity as needed or desired to isovolumetrically sphere the cells, taking into consideration the surfactant selected.

Some surfactants and detergents that also permeabilize cells may also be employed for admixture with the sample prior to, or during, incubation. Examples of surfactants include, without limitation, the anionic surfactant ammonium perfluoralkyl carboxylate (commercially available as Fluorad® FC-143 (3M Company, Minneapolis, Minn.)), sodium lauroyl myristoyl lactylate (commercially available as Pationic® 138C (R.I.T.A. Corp, Woodstock, Ill.)), or from the non-ionic surfactants Dodecyl-α-D-maltoside, N,N-bis[3-D-glucon-amidopropyl)cholamide, polyoxypropylene-polyoxyethylene block copolymer, N-tetradecyl-α-D-maltoside, Daconyl-N-methyl-glucamide, n-Dodecyl-α-D-glucopyranoside, n-Decyl-α-D-glucopyranoside, polyethylene glycol ester of stearic acid, ethoxylated cocomonoglyceride, octyphenoxypoly(ethyleneoxy)ethanol, ethoxylated octylphenol, and linear alcohol, or, from among the cationic surfactants, coco hydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosul fobetaine, N-dodecyl-N,N-dimethyl-3-ammonio-1-propanesulfonate, N-tetradecyl-N,N-dimethyl-3-ammonio-1-propanesulfonate. Examples of detergents include, without limitation, non-ionic detergents.

Other cell permeabilizing agents can also be included in various embodiments of the method to permit cell impermeant dyes to permeate the cell membrane. Desirably, these components are used at a concentration between about 0 to about 1% of the total composition.

In still alternative embodiments of the rapid staining method, for a sample that contains cells that are not permeable to the ligand(s) and dye, the sample is contacted prior to or during incubation with the ligand and dye with at least one cell lysing reagent that differentially lyses non-nucleated cells present in the sample and conserves the platelets and nucleated cell populations. The nucleated cell populations comprise nucleated red blood cells and leukocytes. A differential lysing of the non-nucleated cells in the sample/reaction mixture and an optional quenching of the lysing reaction without altering the intrinsic or extrinsic properties of the nucleated cells, particularly the platelets may occur before or as part of the incubation of the sample with the dye and ligand(s).

The lytic system is employed typically where the nucleic acid dye is an impermeant dye. In some embodiments, a lytic system can include a single lytic reagent. In other embodiments, the lytic system includes two reagents, such as a lytic agent and a quench reagent. In some embodiments, a lytic system can include three reagents, a lytic agent, a quench reagent and a fixation reagent.

The lytic reagent(s) include, but are not limited to: ERYTHROLYSE II reagent (Beckman Coulter, Inc.), the lysing reagent disclosed in U.S. Pat. No. 5,882,933, incorporated by reference for the purposes of identifying the reagents. The lytic systems useful in the methods described herein can include a second reagent, e.g., one that quenches or retards the effect of the lytic reagent during the remaining steps of the method, e.g., while the sample flows through the aperture in the transducer module. A useful lytic retarding agent may be selected depending upon the lysis agent and may likely be employed only where speed is an issue. An example of such a lytic retarding agent is Stabilyse™ reagent (Beckman Coulter, Inc.). The lytic retarding reagent can vary provided that the primary requirement of quenching of the lytic reaction as well as the conservation of the antigenic determinants and desired electrical and optical properties on the cells of interest are accomplished. Other lytic systems are marketed commercially and include the Immunoprep™ system (U.S. Pat. No. 5,030,554; Beckman Coulter, Inc.), the Versalyse™ system, the Facslyse™ system (Becton Dickenson), or an ammonium chloride system. These systems are useful in the methods described herein.

In one embodiment, the incubation involves a lyse/quench reaction, which involves contacting a portion of the sample/antibody mixture with a lytic system or lytic reagent, as defined above, for about 4 to 10 seconds. After several seconds, the effect of the lytic system is then retarded or quenched with a quenching reagent as described and the RBCs are lysed. The quenching reagent generally is in contact with the sample, while the sample flows through the aperture in a cytometry/hematology analyzer. This second reagent is thus in contact with the mixture for at least a few seconds. A conventional fixation reagent may also be employed depending upon the choice of lytic reagents or the preferred implementation of the method. Volumes of lytic reagent, quench reagent, and fixation reagent, if desired, can be readily selected by the person of skill in the art depending upon the identity of the lytic system used.

Among other conditions for the rapid staining and incubation is the order of addition of the reagents to the sample. In one embodiment, the ligand(s)/antibody(ies) are first added to the sample, followed by the nucleic acid dye, followed by the other components. The single reaction mixture is then contacted with an optional lytic reagent that differentially lyses non-nucleated red blood cells present in the sample and conserves the platelet populations in the sample and/or with the sphering reagent. Finally, the optional quenching or fixative reagents may be added. Alternatively in another embodiment, the lytic reagent or sphering reagent is added first to the sample, prior to addition of the ligand(s) and dye. In still another embodiment, all reagents are added simultaneously. Due to the rapidity of the rapid staining, the latter process of adding all reagents substantially simultaneously is preferred.

The incubation of the reaction mixture and lytic and quenching cycles (which may occur before or during the incubation with the ligand/dye reagents) is preferably filly automated.

B. Parameter Measurement and analaysis

Methods for the rapid identification and analysis of platelet populations, both normal and atypical, and particularly immature, reticulated platelets, in a biological sample are performed using the above-defined rapidly stained sample/dye/ligand(s) reaction mixture and the following steps. Preferably, the methods are filly automated, although several steps may be performed manually, if necessary.

Following the rapid staining and incubation, the resulting sample/ligand/dye reaction mixture is passed through a sensing region in a cell analyzer, e.g., a single flow aperture in transducer of a multiparametric high throughput flow hematology analyzer or flow cytometer. The transducer is capable, in a single analytical step, of making multiple correlated measurements (electrical, fluorescent and optical) on cells as they pass through a single aperture in the transducer module. The cytometer measures multiple parameters. The sample is analyzed using the data generated by these measurements. Generally, data generated by measurement of at least two parameters enables detection or quantitative detection of the label on the anti-platelet ligand, e.g., fluorescence of the label conjugated or attached to the selected ligand, and detection of the signal being emitted by the nucleic acid dye, e.g., fluorescence. Additional parameters may be measured and analyzed in combination with the two parameters mentioned above. In one embodiment, the passing step is a single step that measures the mixture for multiple (at least two) different parameters. The sensing region of a flow cytometer irradiates the incubated sample with a laser light source. The parameters may be the same or different and include one or more channels of fluorescence, one or more optical parameters, one or more electrical parameters, or combinations thereof, depending upon the identity of the label on the ligand and the signal emitted by the dye. Thereafter, each cell population is identified and enumerated by using at least two of these parameters which are light scatter, direct current, axial light loss, opacity, radio frequency, or fluorescence are measured for the sample.

For example, in one embodiment, the fluorescence of a cell is preferably measured within discrete, multiple wavelength ranges, which are determined by the respective fluorescence emission spectra of the dyes or fluorochromes used to label the antibodies which bind the platelets and other cells in the sample. Thus, fluorescence analysis is combined with at least one simultaneously-measured electrical or optical measurement made on each individual cell as it passes through the transducer to identify a cell population. In this manner, the platelet populations are obtained without the need for further separation of the lysed and unlysed fractions, if present, in the sample, or for correlation of different measurements made on different cells in the sample in different transducers.

In one embodiment, the fluorescence analysis permits the identification of platelets bound by the fluorescently-labeled platelet-specific antibody from non-platelets in the sample, and permits the identification of at least one platelet population. In another embodiment, measurement of the fluorescence of the nucleic acid dye permits identification of the immature platelets. The advantage of a more accurate measurement of platelet populations occurs when the anti-platelet antibody fluorescence is performed to isolate and identify a pure population of platelets from other debris, following by use of the nucleic acid dye fluorescence to identify immature platelet populations in the pure platelet population. This can be seen in the figures described herein.

Additional parameters include an optical parameter, e.g., generally one of light scatter, e.g., side scatter or forward light scatter. However, measurement using only light scatter is not preferred as it is less accurate in measuring certain platelet populations (see the figures). More than one angle of light scatter may be used where only a single fluorochrome is employed. The angle of light scatter may be selected from between about 10 to 70 degrees of light scatter, i.e., medium angle light scatter (MALS); between about 10 to 20 degrees of light scatters, i.e., lower medium angle light scatter (LMALS): between about 20 and about 70 degrees, i.e., upper medium angle light scatter (UMALS) or between about 80-100 degrees of light scatter, nominally orthogonal, i.e., side scatter (SS), low angle forward light scatter between about 2-18 degrees, and axial light loss or absorbance.

The electrical parameter is generally direct current electrical impedance measurement of volume (DC). Alternatively, the electrical parameter can be opacity, which is calculated as the radio frequency of the cell over the DC volume. These parameters are discussed and defined in detail in commonly assigned U.S. Pat. No. 5,125,737, which is incorporated herein by reference.

The above-described flow cytometric steps may be performed manually, partly manually and partly automated, or completely automated. One such automated flow cytometry instrument is described in U.S. Pat. No. 6,228,652, incorporated by reference herein, which discloses an automated instrument by which all of the aforementioned cell characteristics, i.e., DC volume, RF conductivity (opacity), light scatter and fluorescence characteristics, can be determined simultaneously, thereby obviating any need to correlate data gathered from separate transducers. The electrical measurements consist of DC (direct current volume/impedance) and RF (radio frequency). The optical measurements include light scattering and fluorescence. The light scatter measurements may consist of multiple angles of scatter collected on each cell to include low, medium and high forward angle measurements as well as right angle (90 degree/side scatter) measurements. The fluorescence measurements are made by collecting the fluorescence emission on two or three photomultiplier tubes or detectors (PMT).

Desirably useful in performing the analysis of the various embodiments are hematology instruments that measure electrical, optical and fluorescence parameters. See e.g., the instrument described in U.S. Pat. No. 6,228,532, incorporated herein by reference. In an exemplary embodiment, a 532 nm green diode laser is used as the illumination source in a usefull flow hematology system. However, for one skilled in the art, lasers with alternative emission lines, e.g., red laser such as 633 nm or 647 nm laser, blue lasers such as a 488 nm laser or violet lasers such as a 405 nm laser, can be substituted and the fluorochromes adjusted appropriately. Dyes may be tailored to the laser system.

The resulting data provides the information required to identify and optionally quantify one or more of the platelet populations or subpopulations identified above. Other non-platelet cells may also be identified. According to this method, each cell population is identified by at least two parameters, taking advantage of differing patterns of expression detectable in the fluorescence analysis of the fluorescence in the single reaction mixture. For example, the two parameters may be a channel of fluorescence identifying the anti-platelet ligand fluorescence and an optical parameter, such as side scatter. Another two parameters that may be used to identify a cell population may be two channels of fluorescence. Another two parameters that may be used to identify a cell population may be a channel of fluorescence and an electrical parameter, e.g., DC. Another two parameters that may be used to identify a cell population may be an optical parameter, e.g., SS, and an electrical parameter, e.g., DC. Additional combinations of the measurements made on the single reaction mixture are obvious to one of skill in the art, depending upon the particular fluorochromes, dyes, antibodies, optical and electrical parameters used in this method. These analytical steps are desirably incorporated into algorithms in an automated process.

C. Population Differentiation

According to this assay method, a platelet population, such as immature, reticulated platelets, is distinguished from admixture with one or more populations which may also be present in the sample, including white blood cells, reticulated red blood cells, immature reticulocytes, cellular debris and non-cellular aggregates. Similarly, the assay method allows more than one platelet population to be identified. These platelet populations in the sample are identified upon review of histograms generated from the measured data, plotting one parameter against the other.

In one embodiment, a platelet population is differentiated from other blood cells, cellular debris and non-cellular aggregates by anti-platelet fluorescence. In another embodiment, mature platelets are distinguished from immature platelets by size and granularity as measured by the parameters of light scatter and anti-platelet fluorescence. In still another embodiment, reticulated platelets are distinguished from mature platelets by measuring fluorescence of the nucleic acid dye. In still another embodiment, anti-platelet fluorescence is employed to identify the platelet population, and that population is then itself further analyzed using nucleic acid dye fluorescence to obtain accurate measurements and identification of the immature platelet population.

In one embodiment the parameters used for this evaluation include forward and side scattered light and a minimum of at least two channels of fluorescence. The fluorescence emission pattern in each of the collected channels is representative of either the dye alone, the fluorochrome conjugated monoclonal antibody alone, or the spectral addition of the dye and at least one of the fluorochrome conjugated monoclonal antibodies in the reaction mixture. However, the method might also employ the VCS parameters of impedance (DC) and conductivity (RF) along with light scatter and fluorescence measurements. As indicated above, a number of suitable lasers may be employed to excite the fluorescence, including a 488 nm blue argon laser, a green 532 nm laser, or a red laser (633 nm, 635 nm, 640 nm or 644 nm) if the dye is a red excitable dye used in combination with antibodies conjugated to red excitable fluorochromes.

Where the peak emission spectra of at least one fluorochrome label(s) on at least one antibody/ligand in the mixture overlaps the dye emission spectra to form a new spectral pattern that is non-compensatable, the resulting fluorescence signals detected in any channel of the detection system are characteristic of either the fluorescence emission of the dye alone, the fluorochrome conjugated antibody(s) alone, or the non-compensatable product of the additive fluorescence of the dye and at least one fluorochrome conjugated antibody(s).

The following Table I illustrates the parameters that may be used in gating procedures to identify and distinguish the following platelet populations and subpopulations from each other using the method. The parameters selected are related to the identity of the ligand and its label and the particular nucleic acid dye, and lasers employed in the analyzer. The relationship of the parameters to the choice of labeled ligands and nucleic acid dyes, and lasers are readily known and selected by one of skill in the art given the teachings provided herein. As indicated in Table I, sets of two parameters may be used to identify certain cell or platelet subsets in the method of this invention employing a nucleic acid dye, e.g., AO, and a desired fluorochrome labeling the selected ligand, e.g., PE-Cy7. In one embodiment, Table I is useful to identify those pairs of parameters that can be employed to distinguish, or gate, between any two of the cell types indicated in the method described herein. One would use a set of parameters that are in common between the two cell types. For example, in one embodiment of a method described herein, if one selected the cell types of mature platelets and platelet satellites for identification, one could use a set of parameters in common between the two cell types as stated in the table, e.g., the set of forward scatter and fluorescence.

TABLE I

| CELL TYPE IN SAMPLE | IDENTIFYING PARAMETERS |
| --- | --- |
| mature platelets | Forward Scatter and Anti-Platelet Fluorescence, Side Scatter and Fluorescence, Direct Current and Opacity, Opacity and Fluorescence, Direct Current and Radio Frequency, Direct Current and Fluorescence, Radio Frequency and Fluorescence, Axial Light Loss and Fluorescence; Forward Scatter and Side Scatter |
| immature reticulated platelets | Forward Scatter and Nucleic Acid Dye Fluorescence, Side Scatter and Fluorescence, Direct Current and Fluorescence, Radio Frequency and Fluorescence, Opacity and Fluorescence, Axial Light Loss and Fluorescence, |
| giant platelets | Forward Scatter and Side Scatter, Forward Scatter and Fluorescence, Side Scatter and Fluorescence, Direct Current and Radio Frequency, Direct Current and Opacity, Direct Current and Fluorescence, Radio Frequency and Fluorescence, Axial Light Loss and Fluorescence |
| platelet clumps | Forward Scatter and Side Scatter, Forward Scatter and Fluorescence, Side Scatter and Fluorescence, Direct Current and Radio Frequency, Direct Current and Fluorescence, Direct Current and Opacity, Radio Frequency and Fluorescence, Axial Light Loss and Fluorescence. |
| platelet satellites | Forward Scatter and Fluorescence, Side Scatter and Fluorescence, Direct Current and Radio Frequency, Direct Current and Fluorescence, Radio Frequency and Fluorescence, Axial Light Loss and Fluorescence |
| activated platelets | Forward Scatter and Fluorescence, Side Scatter and Fluorescence, Direct Current and Radio Frequency, Direct Current and Fluorescence, Radio Frequency and Fluorescence, Axial Light Loss and Fluorescence |
| total platelet population. | Forward Scatter and Side Scatter, Forward Scatter and Fluorescence, Side Scatter and Fluorescence, Direct Current and Radio Frequency, Direct Current and Opacity, Direct Current and Fluorescence, Radio Frequency and Fluorescence, Axial Light Loss and Fluorescence |
| white blood cells or red blood cells | Forward Scatter and Side Scatter, Forward Scatter and Fluorescence, Side Scatter and Fluorescence, Direct Current and Radio Frequency, Direct Current and Opacity, Direct Current and Fluorescence, Radio Frequency and Fluorescence, Axial Light Loss and Fluorescence |
| reticulated red blood cells | Forward Scatter and Fluorescence, Side Scatter and Fluorescence, Direct Current and Fluorescence, Radio Frequency and Fluorescence, Axial Light Loss and Fluorescence |
| immature reticulocytes | Forward Scatter and Fluorescence, Side Scatter and Fluorescence, Direct Current and Fluorescence, Radio Frequency and Fluorescence, Axial Light Loss and Fluorescence |
| cellular debris | Forward Scatter and Fluorescence, Side Scatter and Fluorescence, Direct Current and Fluorescence, Opacity and Fluorescence, Radio Frequency and Fluorescence, Axial Light Loss and Fluorescence |
| non-cellular aggregates | Forward Scatter and Fluorescence, Side Scatter and Fluorescence, Direct Current and Fluorescence, Opacity and Fluorescence, Radio Frequency and Fluorescence, Axial Light Loss and Fluorescence |

This method further involves quantifying, as well as identifying, a platelet population in the sample. In one embodiment the total platelet population in the sample, which includes mature platelets, immature reticulated platelets, giant platelets, platelet clumps, and platelet satellites is quantified more accurately than can be accomplished using other known platelet measurement assays.

In one embodiment, the method involves adding to a human plasma sample of about 1 to 100 µL, an anti-platelet antibody labeled with phycoerythrin coupled to cyanine 7 (PE-Cy7) and the nucleic acid dye Acridine Orange. PE-Cy7 has emission bandwidths beyond that of the metachromatic Acridine Orange. These emission spectra enable selection of dye and label for the simultaneous use in this method. Further, the absence of DNA in platelets reduces the intensity of the dye's broad emission and consequently increases the fluorescence signal to noise ratio of the antibody staining. The labeled ligand is added at a volume of from 1 to 50 µl in a concentration which is dependent upon the antibody used and determined by one of skill in the art by conventional titration. The nucleic acid dye is generally added in sphering or other buffer at a concentration of 0.1 to 1.0 µg/ml in a volume of about 0.5 to 2.0 ml. The incubation is performed at room temperature in the presence of an optional sphering agent and for a time of 60 seconds or less following addition of the reagents to the sample. The binding time of the antibody to the surface of the platelets is reduced to within 10 seconds from the normal 10 minutes normally associated with antibody staining of cells. In combination with a fast binding of less than 30 seconds of a metachromatic dye in the presence of a sphering agent (see, e.g., U.S. Pat. No. 6,060,322), this rapid antibody staining method is an unique approach to measuring platelet populations with a metachromatic dye. Following this incubation, the mixture is passed through the sensing region of a flow/hematology analyzer where electrical, optical and fluorescence measurements are obtained. The resulting data is used to determine a mature platelet count, a reticulated platelet count and an immature platelet fraction, among others. This embodiment of the method tacks a physical wash or other step of physical cell separating. Because the method does not employ such additional steps, it is more suitable for rapid performance on an automated system, than are other methods.

In an embodiment of the method in which a platelet-specific antibody is employed as the ligand, the ligand is specific for platelets (or for a population of antibodies if it binds platelet populations differentially) and does not stain other blood components. This characteristic can be used to identify and resolve the platelets from the rest of the blood cells or debris by only acquiring the fluorescence signal from the stained platelets and then measuring the dye fluorescence on this population. This method decreases the measurement time, increases throughput and minimizes the size of the acquired file.

In still another embodiment, the method is useful for reticulated platelet measurement in whole blood. Whole blood is the sample of choice for use in because the platelet component in whole blood is in its natural environment which minimizes any chance of activation or loss of platelets. Because reticulated platelet measurements are more in need in patients with low platelet counts to determine if the condition is one of bone marrow failure or vascular destruction of platelets, a sample with low platelet count will require longer measuring time to have enough counts for a statistically meaningful result. When whole blood is used, the measurement is affected by the enormous numbers of red blood cells present with the platelets. This requires high dilution of the blood sample to prevent coincident counting of a red blood cell with platelet which will lower the reticulated platelet value. Further the data file acquired is enormous due to the inclusion of the large numbers of red blood cells. Therefore, a whole blood sample with low platelet counts in prior art methods will compromise the throughput due to the longer measurement time.

According to the present method, to diminish the effect of red blood cells, the whole blood sample is either lysed to remove the red blood cells or physically separated to remove the platelets from the rest of the blood cell components thereby increasing the proportion of platelets in the sample. Both preparative methods introduce an optional extra step to this embodiment of the method for the measurement of reticulated platelets. For the lyse method, an anti-platelet antibody and nucleic acid dye are added to the whole blood sample followed by the lysing step and resuspension in the sphering buffer to hasten dye binding to the reticulated platelets. The method is then practiced as described above, using selected parameters of forward scatter, side scatter, direct current and fluorescence to identify reticulocytes (immature red cells) simultaneously with mature platelets. See Table I.

The method described herein, and as illustrated in the Examples below by employing the binding of the platelets with a fluorochrome conjugated anti-platelet specific antibody in combination with a nucleic acid dye results in improved resolution and identification of the platelets from the non-platelet population. This method permits more consistent and reliable reticulated platelet values for diseases such as idiopathic thrombocytopenic purpura or other diseases characterized by contaminating red cell fragments that fall within the platelet population, generally leading to a false result. Thus, this assay is useful in diagnosing a disorder based upon an accurate quantification of total platelet population.

In yet another embodiment, various components of the methods described above may be combined in kits for ready practice of this method on automated instruments. Thus combinations of dyes, ligands and labels that have never been combined for use may form compositions useful in the practice of these methods.

EXAMPLES

The following examples illustrate various aspects of the rapid staining method for the identification and quantification of platelet populations in biological samples. These examples do not limit the scope that is defined by the appended claims.

Example 1

Method of Identifying and Staining for Reticulated Platelets

A. Sample Preparation i. The Rapid Staining Preparation

For each of the studies discussed herein and illustrated in the figures, a fluorochrome conjugated anti-platelet antibody, e.g., anti-CD41 (0.5 µg/mL) or anti-CD61 (0.5 µg/mL) was added to an aliquot of human whole blood (about 25 µL). The label conjugated to each antibody ligand was the fluorochrome, phycoerythrin-cyanine-7 (PeCy-7). Conjugation was by conventional means. Each antibody/sample mixture was incubated at ambient temperature for not more than 10 seconds.

Where appropriate for the samples described below and in the figures, an aliquot of the antibody stained sample (about 2 µL) was then added to the metachromatic nucleic acid dye Acridine Orange (0.1-1.0 µg/mL) in sphering buffer (0.5 to 2.0 mL), mixed and immediately measured. The entire reaction from antibody binding to nucleic acid staining was complete in less than 60 seconds.

ii. Comparative Sample Preparations

Other samples used in the experiments were either not admixed with anti-platelet antibody, or admixed in a similar fashion with non-specific antibody (an isotype antibody conjugated with the same fluorochrome) or mixed with AO only in the proportions described above. Such samples were used for comparison with the samples prepared by the rapid method described B. Analysis For performance of one analysis, blood specimens were prepared from samples from a healthy subject by staining with a nucleic acid dye, Acridine Orange, and no antibody. The "test" specimens were prepared from the same subject as described in Part A above.

An aliquot of each sample (about 1-2 ml) was introduced into an F500 flow cytometer (Beckman Coulter) and multiple fluorescent, optical and electrical parameters were measured. Data produced thereby was analyzed to produce the histograms identified in the figures. In histograms identifying a platelet population by evaluation of two parameters, as described, that platelet population was further evaluated using another two parameters to identify subsets of platelets.

The histograms of the figures illustrate the rapid antibody staining method with an anti-platelet antibody to identify, resolve and enumerate the platelets from any debris present in the platelet population (P) in both healthy volunteer samples and a clinical sample of thrombocytopenia. The histograms (all two-parameter) reported herein compare results with prior art methods using evaluation of light scatter only or other combinations to identify plates.

In a first experiment, a healthy subject sample was stained with the metachromatic dye Acridine Orange (AO), but not with an anti-platelet antibody, according to sample preparation described above. A conventional gating strategy for identifying and enumerating platelets employed light scatter parameters, e.g., size/forward scatter (FS) vs. granularity/side scatter (SS) to identify cellular populations. The resulting histogram (FIG. 1A) showed the separation of the platelets (P), red blood cells (RBC) and white cells (WBC) based on size (FS) and granularity (SS). The platelets were the lowest population (P) with an oblong shape. When the same sample preparation was evaluated using the parameters of FS and PECy7 fluorescence, the platelets were not stained with an anti-platelet antibody and therefore the resulting histogram (FIG. 1C) is devoid of any platelets, i.e., no fluorescence was detected. When the same sample preparation was evaluated using the parameters of FS vs. nucleic acid dye fluorescence, the resulting histogram showed the size and fluorescence of red blood cells, white blood cells, and platelets including reticulated platelets. The platelets appeared as an arc and were well separated from the rest of the cells. The red cells had lower fluorescence than platelets. The white cells, having DNA, were off scale and seen as vertical lines (WBC) on the top right hand corner of the histogram of FIG. 1E. The reticulated platelets, as indicated, were the brighter fluorescent population in the platelet population.

Figure 1B:
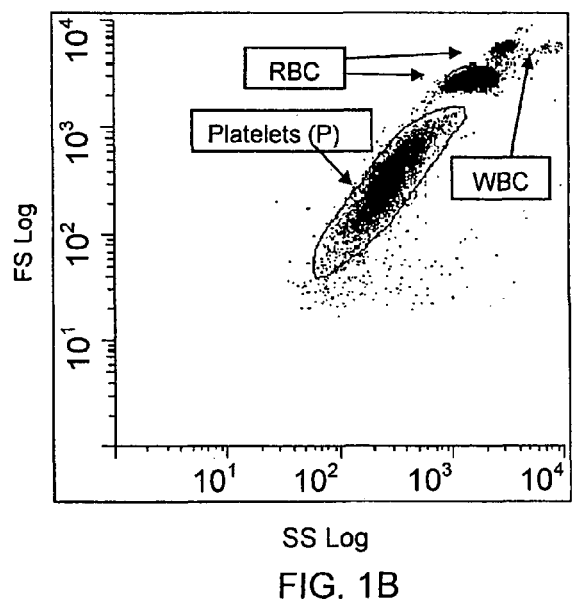
Figure 1C:
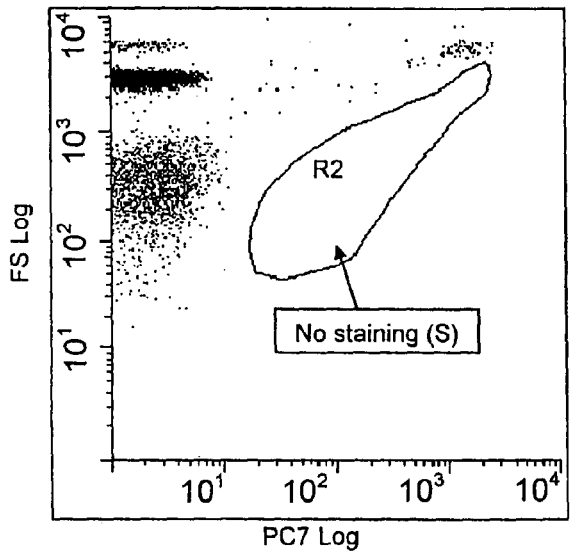
Figure 1D:
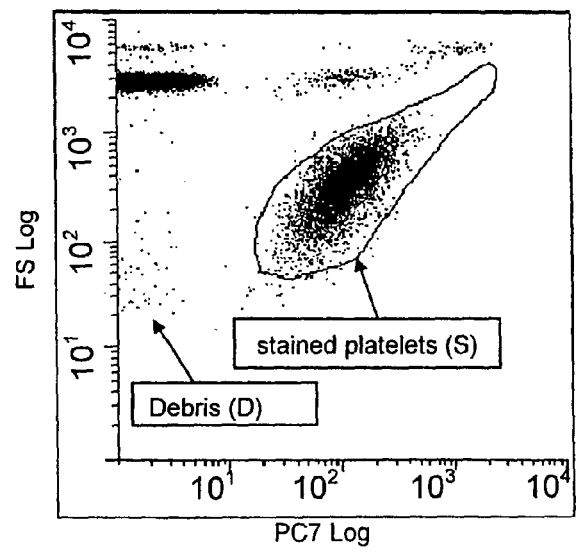
Figure 1E:
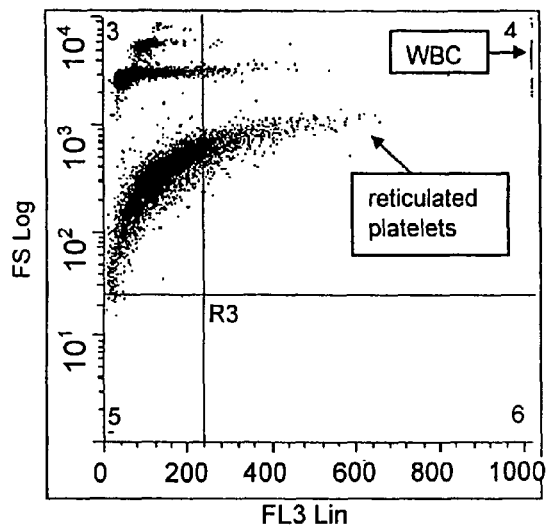

When the same subject's blood sample was prepared according to the method of Part A above using with PECy7 fluorescent-labeled anti-CD41 anti-platelet antibody and AO in the rapid staining method, a similar separation of the platelets (P), RBCs and WBCs based on size (FS) and granularity (SS) are detected (FIG. 1B). When the parameters of FS v. anti-platelet fluorescence were employed on this sample that had been subjected to the rapid antibody staining method using PECy7 fluorescent-labeled anti-CD41 anti-platelet antibody that emits in the 760-820 nm range and AO, the resulting histogram displayed a different result. FIG. 1D displayed the size and fluorescence of the platelet population in which the platelets were bound with CD41-PECy7 anti-platelet antibody. The platelets in this histogram appeared as a distinct fluorescent population (S). Particles that were not platelets were non-fluorescent and appeared separate from the platelet population as debris. This latter area is increased in patients with low platelets and certain disease states and illustrates the importance of this method for specifically distinguishing platelets from non platelet events.

Figure 1F:
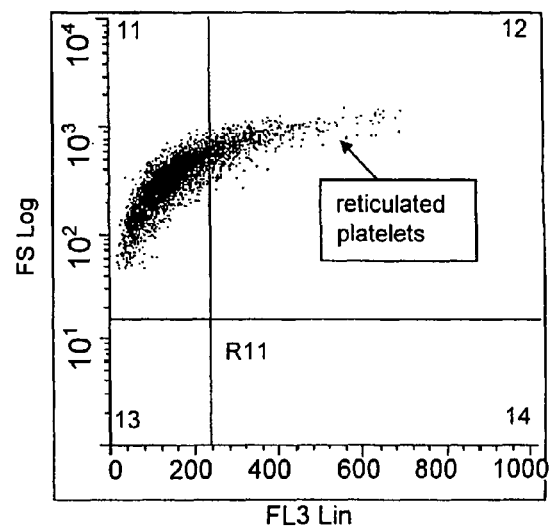

Subsequent analysis of the identified platelet population identified in the histogram of FIG. 1D was made by the parameters of FS vs. nucleic acid dye fluorescence. Because the histogram of FIG. 1F gated on the pure population of platelets devoid of debris and other cells that had been identified and resolved by anti-platelet antibody staining, more accurate enumeration of platelets and reticulated platelets resulted. The reticulated platelets, which are the immature platelets, were larger in size as demonstrated by forward scatter and brighter in AO fluorescence due to the presence of platelet reticulum or granules.

Figure 2A:
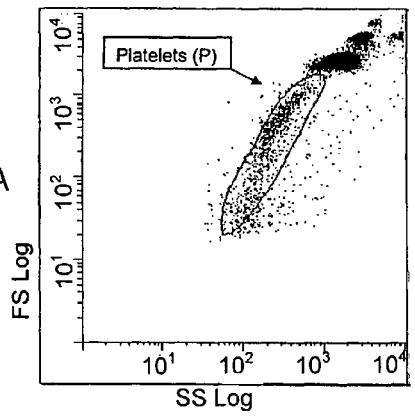
FIGS. 2A-2D are two parameter histograms of samples from a healthy patient whose blood specimen was prepared for analysis by admixture and incubation with an anti-platelet antibody (anti-CD41-PECy7) and AO, using the rapid staining methods described herein.
Figure 2B:
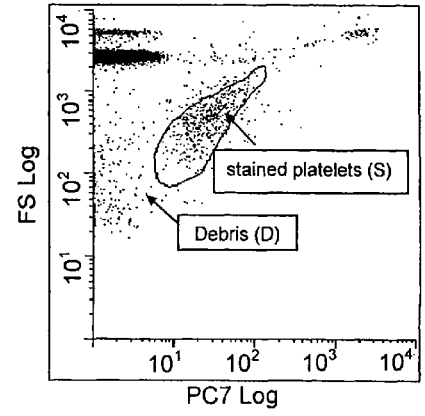
Figure 2C:
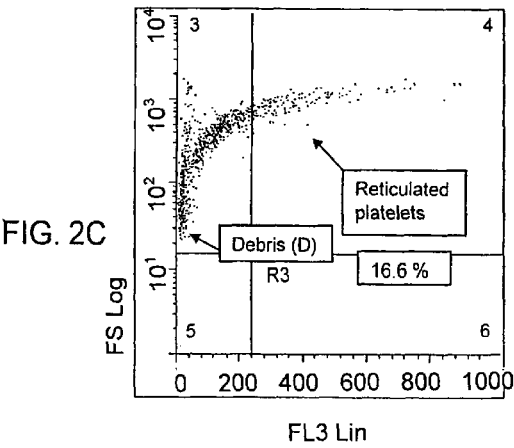

In a second experiment, a blood sample from a healthy patient was prepared for analyses by admixture and incubation with an anti-platelet antibody (anti-CD41-PECy7) and AO, using the rapid staining methods described above. Cytometric evaluation using light scatter only, i.e., forward scatter (FS) vs. side scatter (SS) provided a histogram identifying the platelet population (FIG. 2A). A subsequent analysis gating on the platelet population identified in FIG. 2A using FS vs. AO fluorescence (FIG. 2C) produced a histogram showing reticulated platelets (immature) measured at about 16.6% of the total platelet population.

Figure 2D:
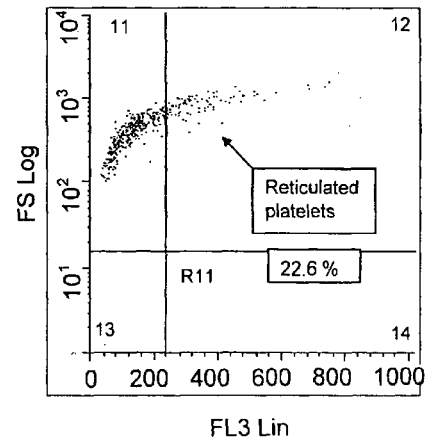

Analysis of the same sample using the parameters of FS vs. anti-platelet antibody fluorescence produced a histogram (FIG. 2B) displaying a separation of the stained platelets from the debris and other cells. Therefore a subsequent analysis, gating on the pure platelet population as previously identified as "S" in the histogram of FIG. 2B, which excluded debris, used the parameters of FS vs. AO fluorescence. In this case, the exclusion of debris allowed the parameters of the histogram of FIG. 2D to provide improved resolution of platelets. A higher percentage of reticulated platelets, i.e., 22.6%, resulted in contrast to the 16/6% obtained by FIG. 2C. The use of size (FS) and granularity (SS) parameters included debris in the calculation leading to lower percentage of identified reticulated platelets, then that provided by use of the rapid staining method coupled with analysis using anti-platelet fluorescence with nucleic acid fluorescence. These histograms thus demonstrate the improvement in accuracy which is an advantage of the method described herein.

Figure 3A:
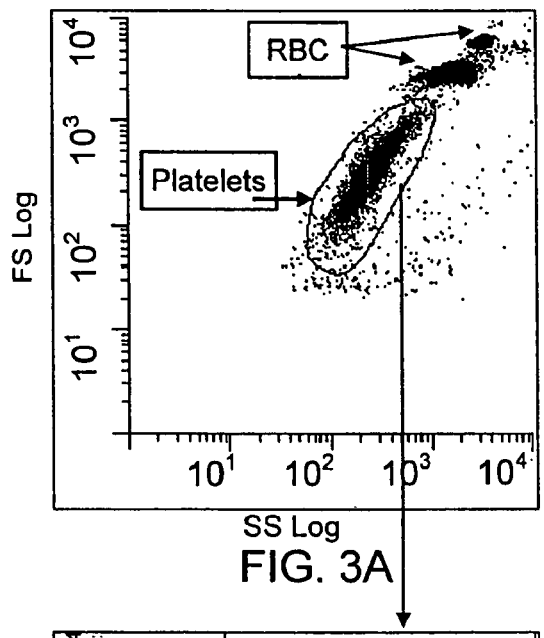
FIGS. 3A-3D are two parameter histograms similar to those shown in FIGS. 2A-2D of samples from another healthy patient whose blood specimen was prepared for analysis according to the rapid staining method (admixture and incubation with anti-platelet antibody and nucleic acid dye) described herein.

In a third experiment, blood samples from another healthy subject were prepared according to the rapid staining method (admixture and incubation with anti-platelet antibody and nucleic acid dye) described in Part A above. The samples were analyzed using forward scatter (FS) vs. side scatter (SS) (FIG. 3A), followed by analyzing the platelet population identified thereby with FS vs. AO fluorescence (FIG. 3C). This analysis provided an estimate of the reticulated platelet population of 23.0%.

Figure 3B:
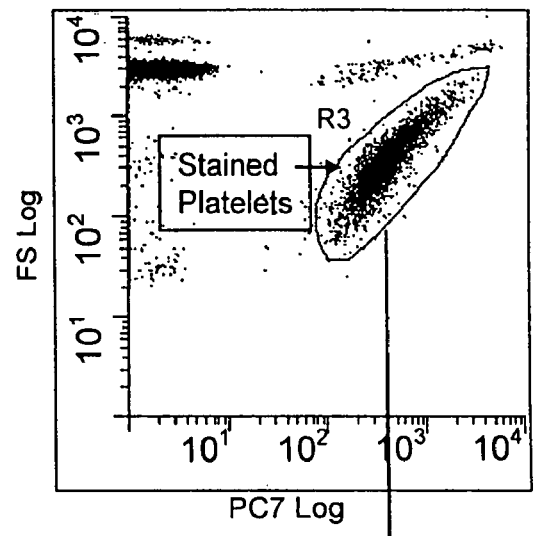
Figure 3C:
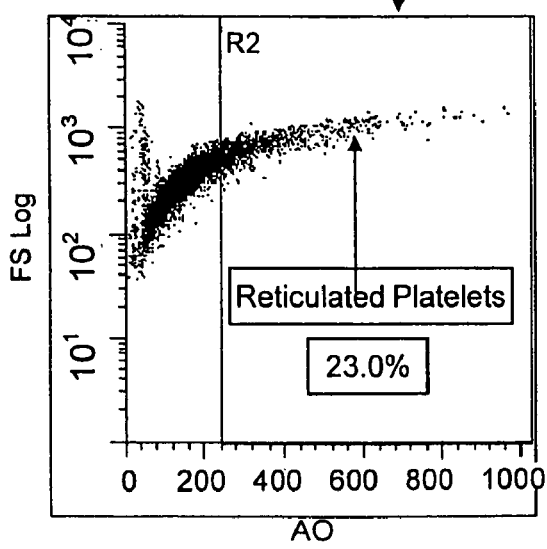
Figure 3D:
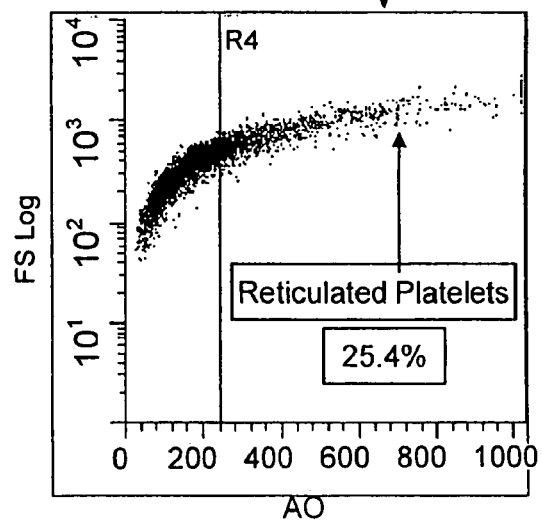

When the same sample was analyzed using FS vs. anti-platelet antibody fluorescence, the pure population of stained platelets were separated from the debris and other cells on the histogram (FIG. 3B). Subsequent gating on this platelet population using FS and AO fluorescence (FIG. 3D) provided a more accurate, higher percentage of reticulated platelets, i.e., 25.4%, for the same patient sample. This experiment illustrated improved identification and enumeration of platelets and reticulated platelets when the platelet population is resolved with a fluorescent conjugated anti-platelet antibody and a nucleic acid dye in a rapid staining method and evaluated according to the present invention.

Figures 4A, 4B, 4C, 4D, 4E, 4F:
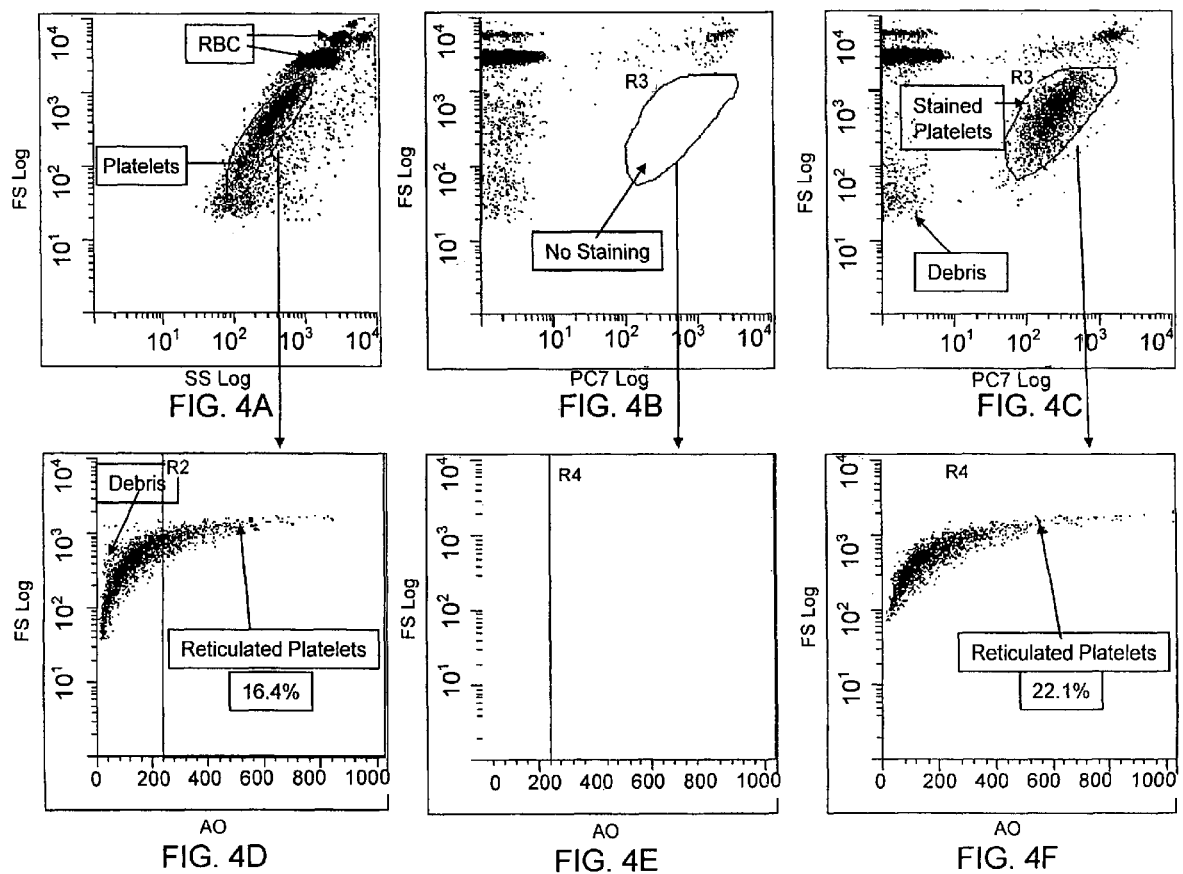
FIGS. 4A-4F are two parameter histograms of samples from the same healthy patient whose blood specimen was prepared for analysis according to the other prior art methods or using the rapid staining methods described herein using anti-platelet antibody and nucleic acid dye. These histograms illustrate the rapid antibody staining method with an anti-platelet antibody to identify, resolve and enumerate the platelets from any debris present in the platelet population (P) in a healthy volunteer sample and compare the results with prior art methods.

In a fourth experiment, samples were prepared from another healthy subject. Each sample was prepared for analysis either using the rapid staining methods described in Part A above using anti-platelet antibody and nucleic acid dye or prepared as alternatively described below. The resulting histograms illustrated that the rapid antibody staining method with an anti-platelet antibody and subsequent fluorescence analysis permits the identification, resolution and enumeration of the platelet population from debris present in the sample, and hence a more accurate platelet population measurement. One sample prepared without any antibody but with AO was evaluated by plotting forward scatter (FS) vs. side scatter (SS), and its histogram showed a separation of the platelets, red blood cells and white cells. The platelets were the lowest population (P) with an oblong shape (FIG. 4A). Resulting gating on that platelet population with FS and AO fluorescence provided a reticulated platelet population of about 16.4% (FIG. 4D).

A second sample was prepared with a fluorescent antibody with no specificity for platelets. Resulting evaluation with the parameters of FS and PC7 fluorescence produced a histogram that did not identify a platelet population (FIG. 4B). Because there was no identified population on which to gate, the histogram showing the subsequent gating with FS and AO fluorescence was blank as well (FIG. 4E).

In contrast, a sample prepared using the rapid staining method of Part A above with PECy7 fluorescent-labeled anti-CD41 anti-platelet antibodies that emit in the 760-820 nm range and AO was then put through the cytometric analyzer. A histogram (FIG. 4C) displaying FS vs. anti-platelet (PC7) fluorescence revealed a platelet population distinct from particles in the sample that were not platelets. The non-platelet or debris area was thus increased in events when a patient sample stained with the antibody is measured. Subsequent gating on that pure platelet population was accomplished and analyzed using FS vs. AO (FIG. 4F). Because the platelet population was identified and resolved by anti-platelet antibody staining in FIG. 4C, it allowed for accurate enumeration of reticulated platelets by relating to the pure platelet population. The reticulated platelets measured in the absence (16.4%, FIG. 4D) and presence (22.1%, FIG. 4F) of anti-platelet specific antibody are similar in a healthy volunteer sample. However, the population is more accurately identified and higher than that of FIG. 4D.

A fifth experiment used blood samples obtained from a patient having mild thrombocytopenia. All samples were prepared according to the rapid staining method described in Part A above, with one anti-platelet antibody (anti-CD41 or anti-CD61) and the nucleic acid dye, AO or with both anti-platelet antibodies and AO as follows. The resulting FIGS. 5A and 5B revealed that analysis with the parameters of forward scatter (FS) vs. anti-platelet fluorescence of a sample stained with PECy7 fluorescent-labeled anti-CD41 or anti-CD61 anti-platelet antibodies and AO provided similar populations of platelets. Subsequent gating on those platelet populations using FS and AO fluorescence provided relatively similar percentages of reticulated platelets, i.e., 21.5% and 21.9%, respectively (FIGS. 5D and 5E). The same evaluations performed on the sample prepared with both anti-platelet antibodies (FIGS. 5C and 5F) revealed 23.5% reticulated platelets. While use of a single different anti-platelet antibody to identify the platelet population in a sample from the same subject in FIGS. 5D and 5E demonstrate a similar percentage of platelets in the sample, the comparison of FIGS. 5D and 5F show increased reticulated platelet value when the rapid antibody staining method is employed using two anti-platelet antibodies rather than a single anti-platelet antibody.

Example 2

Measuring Reticulated Platelets

Figure 6:
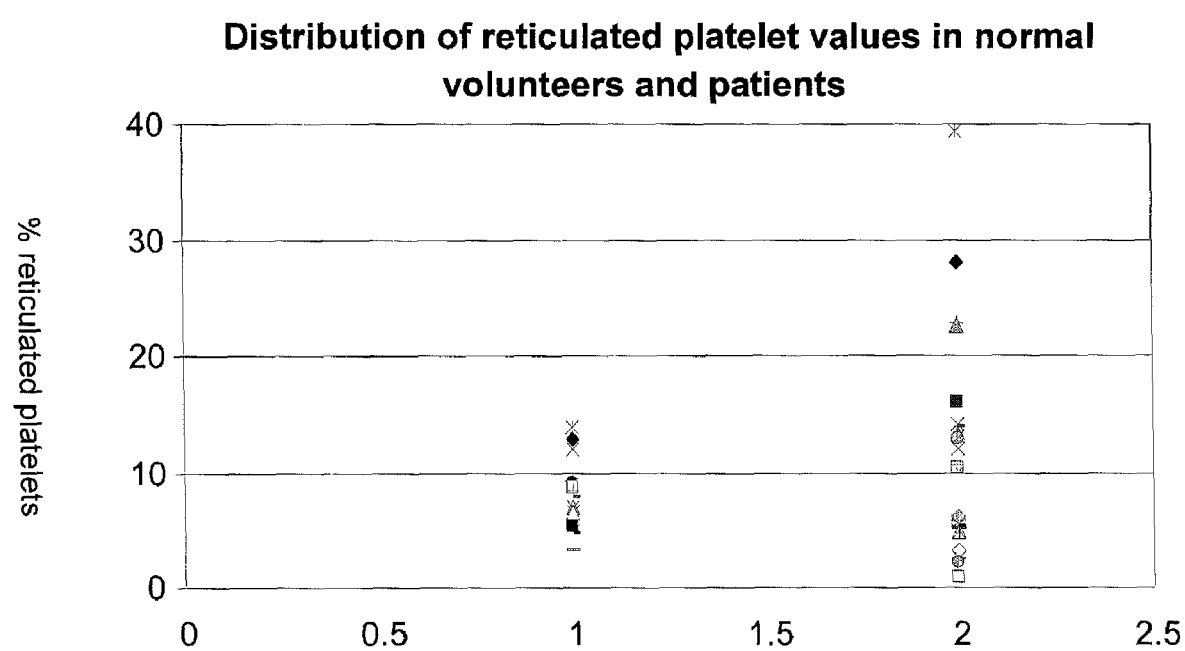
FIG. 6 is a graph illustrating the distribution of reticulated platelet values in normal volunteers and patients. Each symbol represents one individual.

Comparative values in reticulated platelets in normal volunteers and patients: A preliminary study was done with normal volunteers and patients with low platelet counts. Using the method of Example 1 using PE-Cy7-labeled anti-CD41 and Acridine Orange with whole blood samples, the distribution in percentage reticulated platelet values between normal volunteers and patients is distinctly different as shown in FIG. 6. There is a wider spread of values in the patient population.

All published documents, patents and patent applications, as well as the disclosures of the priority documents recited above, are incorporated herein by reference. Numerous conventional modifications and variations of the methods and compositions described herein are included in the above-identified specification and are expected to be obvious to one of skill in the art. Such modifications and alterations to the various embodiments of the invention are believed to be encompassed in the scope of the claims appended hereto.

What is claimed is:

1. A method for identifying a platelet population in a biological sample comprising:
   (a) incubating said biological sample for less than 5 minutes with a nucleic acid dye and at least one labeled anti-platelet ligand, wherein said at least one labeled anti-platelet ligand binds to an epitope, antigen or receptor expressed on both platelets from said platelet population and cells from at least one additional different, non-platelet cell population in said biological sample, and wherein the incubation step is performed under conditions that allow said nucleic acid dye to permeate into the cell and allow said at least one labeled anti-platelet ligand to bind to said epitope, antigen or receptor in less than 5 minutes;
   (b) passing said biological sample through a sensing region of a flow cytometer, wherein said biological sample is irradiated with a laser light source, and measuring fluorescence from said at least one labeled anti-platelet ligand and said nucleic acid dye and at least one additional parameter selected independently from the group consisting of light scatter, direct current, axial light loss, opacity, and radio frequency; and
   (c) detecting or quantifying data generated from said measurements from said at least one labeled anti-platelet ligand, said nucleic acid dye, and said at least one additional parameter, thereby differentiating or identifying said platelet population from said at least one additional different, non-platelet cell in said biological sample.

2. The method according to claim 1, wherein said platelet population identified is a population of immature, reticulated platelets.

3. The method according to claim 1, further comprising (d) quantifying or enumerating one or more platelet subpopulations from said platelet population in said biological sample.

4. The method according to claim 3, wherein said one or more platelet subpopulations is selected from the group consisting of mature platelets, immature, reticulated platelets, giant platelets, platelet clumps, platelet satellites, activated platelets, non-activated platelets, and a combination thereof.

5. The method according to claim 3, wherein said step (c) comprises distinguishing one or more platelet subpopulations from admixture with said at least one additional different non-platelet cell population, said at least one additional different non-platelet cell population including white blood cells, reticulated red blood cells, immature reticulocytes, cellular debris or non-cellular aggregates.

6. The method according to claim 1, wherein step (a) further comprises incubating said biological sample for less than 5 minutes with at least one labeled platelet-specific ligand, wherein said at least one labeled platelet-specific ligand binds to an epitope, antigen, or receptor expressed exclusively on platelets from a platelet population, but not expressed on red blood cells, white blood cells, epithelial cells or endothelial cells, or binds to an epitope that is differentially expressed on platelet subpopulations, and wherein the incubation step is performed under conditions that allow said at least one labeled platelet-specific ligand to bind to said epitope, antigen or receptor in less than 5 minutes.

7. The method according to claim 6, wherein said at least one labeled platelet-specific ligand is labeled with a fluorescent label that (a) has an emission spectrum that is distinguishable from that of said nucleic acid dye; or (b) has an emission spectrum that is distinguishable from, but overlaps with, that of said nucleic acid dye.

8. The method according to claim 7, wherein said nucleic acid dye is Acridine Orange and said fluorescent dye on said at least one labeled platelet-specific ligand is phycoerythrin-cyanine-7 (PECy-7) or PE-Alexa750.

9. The method according to claim 6, wherein said at least one labeled platelet-specific ligand is a monoclonal antibody or a fragment thereof.

10. The method according to claim 1, wherein said at least one labeled anti-platelet ligand specifically binds to an epitope, antigen, or receptor that is expressed on, or differentially expressed on, platelets from said platelet population, and on cells from said at least one additional different non-platelet cell population selected from the group consisting of red blood cells, white blood cells, epithelial cells and endothelial cells.

11. The method according to claim 1, wherein said incubation time is selected from the group consisting of 5 seconds, 10 seconds, 15 seconds, 20 seconds, 30 seconds, 40 seconds, 50 seconds, 1 minute, 1.5 minutes, 2 minutes, 2.5 minutes, 3 minutes, 3.5 minutes, 4 minutes, 4.5 minutes and 5 minutes and any fractional portion therebetween.

12. The method according to claim 1, wherein said at least one labeled anti-platelet ligand is an anti-platelet fluorescent ligand.

13. The method according to claim 1, wherein step (c) comprises differentiating said platelet population from said at least one additional different non-platelet cell population, cellular debris and non-cellular aggregates by detecting or quantifying data generated from said measurement of fluorescence from said at least one labeled anti-platelet ligand.

14. The method according to claim 13, further comprising distinguishing immature, reticulated platelets from mature platelets from said platelet population by analyzing said platelet population using detecting and quantifying data generated from measurement of fluorescence from said nucleic acid dye and said at least one additional parameters of light scatter.

15. The method according to claim 1, wherein the concentration of said nucleic acid dye is about 0.3 to about 2.0 μg/ml in said sample.

16. The method according to claim 1, wherein said biological sample contains (a) platelets from said platelet population and cells from at least one additional different non-platelet cell population in said biological sample that are permeant to said nucleic acid dye or (b) platelets from said platelet population and cells from at least one additional different non-platelet cell population in said biological sample that are rendered permeant to said nucleic acid dye by contact with a sphering agent prior to or during contact with said nucleic acid dye.

17. The method according to claim 1, wherein said nucleic acid dye is selected from the group consisting of a metachromatic dye, a non-metachromatic dye, a blue-excitable dye, a green excitable dye, a red excitable dye, a cell-permeant dye, and a cell impermeant dye.

18. The method according to claim 1, wherein said at least one labeled anti-platelet ligand is a monoclonal antibody or a fragment thereof.

19. The method according to claim 1, which lacks physical washing or other means of separation of said platelet population from said biological sample.

20. The method according to claim 1, wherein said platelet population identified is a population of mature platelets, immature, reticulated platelets, giant platelets, platelet clumps, platelet satellites, activated platelets, non-activated platelets, or total platelets.

21. A kit for identifying a platelet population in a biological sample comprising:
(a) at least one labeled platelet-specific ligand, wherein said at least one labeled platelet-specific ligand binds to an epitope, antigen, or receptor expressed exclusively on platelets from a platelet population, but not expressed on red blood cells, white blood cells, epithelial cells or endothelial cells;
(b) a nucleic acid dye; and
(c) at least one labeled anti-platelet ligand, wherein said at least one labeled anti-platelet ligand binds to an epitope, antigen or receptor expressed on both platelets from a platelet population and cells from at least one additional different non-platelet cell population.

22. A method for identifying a population of immature, reticulated platelets in a biological sample comprising:
(a) incubating said biological sample for less than 5 minutes with a nucleic acid dye and at least one labeled anti-platelet ligand, wherein said at least one labeled anti-platelet ligand binds to an epitope, antigen or receptor expressed on both platelets from a platelet population and cells from at least one additional different, non-platelet cell population in said biological sample, wherein said nucleic acid dye and said at least one labeled anti-platelet ligand emit fluorescence, and wherein the incubation step is performed under conditions that allow said nucleic acid dye to permeate into the cell and allow said at least one labeled anti-platelet ligand to bind to said epitope, antigen or receptor in less than 5 minutes;
(b) passing said biological sample through a sensing region of a flow cytometer, wherein said biological sample is irradiated with a laser light source, and measuring said at least one labeled anti-platelet ligand fluorescence and said nucleic acid dye fluorescence and at least one other parameter selected independently from the group consisting of light scatter, direct current, axial light loss, opacity, and radio frequency; and
(c) detecting or quantifying data generated from said measurements from said nucleic acid dye, said at least one labeled anti-platelet ligand, and said at least one additional parameter, wherein detecting or quantifying data generated from said measurements is based upon identifying a population of platelets using said at least one labeled anti-platelet ligand fluorescence and said additional parameter and gating on said identified population of platelets using said nucleic acid dye fluorescence and an additional parameter, thereby differentiating or identifying said immature, reticulated platelet population in said biological sample.

* * * * *